US009029126B2

(12) United States Patent
Bleyer et al.

(10) Patent No.: US 9,029,126 B2
(45) Date of Patent: May 12, 2015

(54) PROCESS AND METHOD FOR IMPROVING THE WATER REUSE, ENERGY EFFICIENCY, FERMENTATION AND PRODUCTS OF AN ETHANOL FERMENTATION PLANT

(71) Applicants: James Robert Bleyer, Maumee, OH (US); Thomas J Czartoski, Tecumseh, MI (US); Puneet Chandra, Ann Arbor, MI (US)

(72) Inventors: James Robert Bleyer, Maumee, OH (US); Thomas J Czartoski, Tecumseh, MI (US); Puneet Chandra, Ann Arbor, MI (US)

(73) Assignee: Valicor, Inc., Dexter, MI (US)

( * ) Notice: Subject to any disclaimer, the term of this patent is extended or adjusted under 35 U.S.C. 154(b) by 0 days.

(21) Appl. No.: 13/922,497

(22) Filed: Jun. 20, 2013

(65) Prior Publication Data

US 2014/0017728 A1 Jan. 16, 2014

Related U.S. Application Data

(60) Provisional application No. 61/662,019, filed on Jun. 20, 2012.

(51) Int. Cl.
C12N 1/22 (2006.01)
C12P 7/06 (2006.01)
B01D 3/14 (2006.01)
C12P 7/08 (2006.01)

(52) U.S. Cl.
CPC ... C12P 7/06 (2013.01); B01D 3/14 (2013.01); C12P 7/08 (2013.01); Y02E 50/17 (2013.01)

(58) Field of Classification Search
None
See application file for complete search history.

(56) References Cited

U.S. PATENT DOCUMENTS

| | | | |
|---|---|---|---|
| 2,216,904 A | 10/1940 | Brown | |
| 2,216,905 A | 10/1940 | Brown | |
| 2,263,608 A | 11/1940 | Brown | |
| 2,615,029 A | 10/1952 | Rosten | |
| 6,962,722 B2 | 11/2005 | Dawley et al. | |
| 7,608,729 B2 | 10/2009 | Winsness et al. | |
| 7,829,680 B1 | 11/2010 | Sander et al. | |
| 8,481,677 B2 | 7/2013 | Barrows et al. | |
| 2010/0331580 A1* | 12/2010 | Ridgley | 568/840 |
| 2012/0064213 A1 | 3/2012 | Lee | |
| 2012/0121565 A1 | 5/2012 | Willaims | |
| 2012/0208252 A1* | 8/2012 | Brotherson | 435/165 |
| 2013/0165678 A1 | 6/2013 | Kohl et al. | |
| 2014/0053829 A1 | 2/2014 | Lee | |

FOREIGN PATENT DOCUMENTS

| | | |
|---|---|---|
| EP | 2281898 A1 | 2/2014 |
| EP | 2699655 A1 | 2/2014 |
| WO | WO 2012/177922 A2 | 12/2012 |
| WO | WO 2012/145120 A1 | 10/2013 |
| WO | WO 2014/014683 A1 | 1/2014 |

OTHER PUBLICATIONS

Minowa, et al. "Oil Production From Buckwheat Stillage by Thermochemical Liquifaction." Journal of Nire, vol. 2, No. 4, p. 53-62. Jul. 26, 1993. Japan. (Abstract).
Agler, et al. "Conversion of Thin Stillage from Corn-to-Ethanol Dry Mills into Biogas to Offset Natural Gas Consumption." Powerpoint presentation, Mar. 7, 2008.

* cited by examiner

Primary Examiner — Jon P Weber
Assistant Examiner — Teresa E Knight
(74) Attorney, Agent, or Firm — Kohn & Associates PLLC

(57) ABSTRACT

A method of hydrothermally treating stillage by heating stillage to 200 degrees F. to 350 degrees F., altering physicochemical properties of the stillage, enabling facile separation of the stillage, and creating unique product fractions. A method of performing ethanol fermentation by treating stillage to enable facile separation by heating the stillage to a temperature of 200 degrees F. to 350 degrees F., and separating the treated stillage to recover a high protein solids fraction, a stickwater fraction, and an oil fraction. A method of improving fermentation by heating stillage to a temperature of 200° F. to 350° F. resulting in hydrothermally treated stillage, using all or a portion of the hydrothermally treated stillage as a component of a media, and using the media for a process including fermentation and biomass production. Oil, stickwater, high protein solids fraction, high protein meal, metabolites, biomass, and media obtained from the methods above.

43 Claims, 13 Drawing Sheets

FIGURE 10
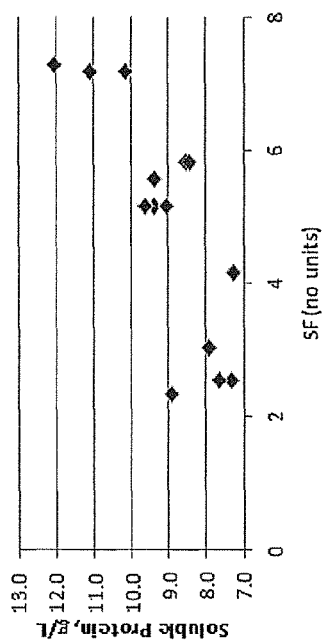
Fig 10A
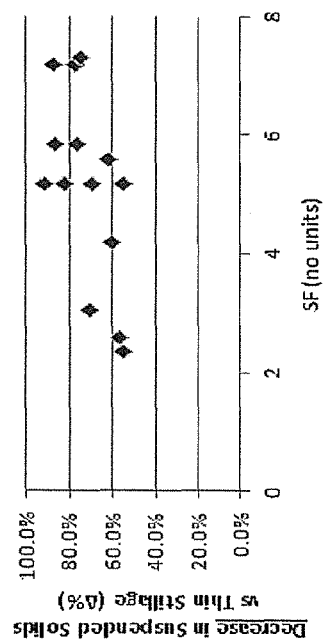
Fig 10B
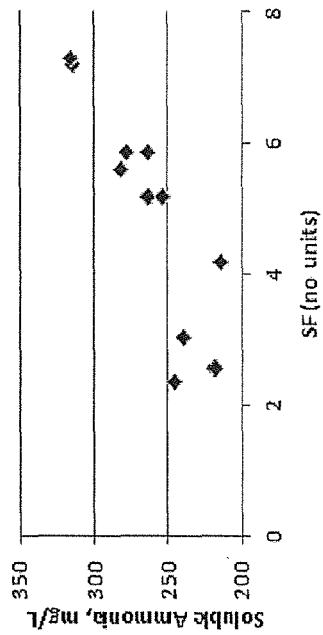
Fig 10C
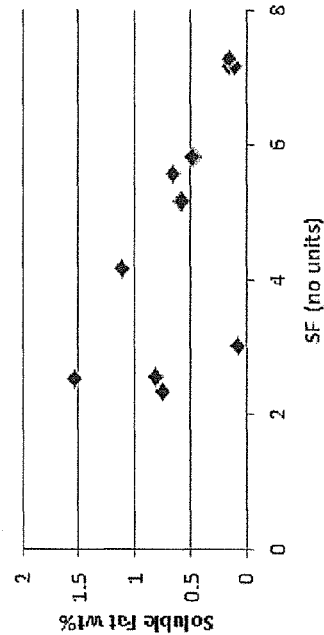
Fig 10D

PROCESS AND METHOD FOR IMPROVING THE WATER REUSE, ENERGY EFFICIENCY, FERMENTATION AND PRODUCTS OF AN ETHANOL FERMENTATION PLANT

BACKGROUND OF THE INVENTION

1. Technical Field

The present invention relates to methods of ethanol fermentation. More specifically the present invention relates to processing stillage.

2. Background Art

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

Ethanol fermentation is the biological process by which sugars are converted into ethanol and carbon dioxide through yeast fermentation. Corn is one of the main feedstock materials used to produce ethanol. Dry milling has previously been used to produce ethanol from corn on other starch sources through fermentation (shown generally in FIG. 1, labeled "Prior Art"). Corn is milled to flour, slurried, and treated with enzymes to convert the starch to sugars. The sugars are converted to ethanol in large fermenters. The ethanol is recovered through a distillation process. The residual spent grains, referred to as whole stillage, contains corn germ, corn bran, corn oil, unconverted starch, unfermented sugars, yeast cells, yeast metabolites, and other suspended and dissolved solids. The whole stillage stream is generally separated into wet distillers grain (WDG) and thin stillage. The wet distillers grains can be dried to produce Dry Distillers Grain (DDG). A portion of the thin stillage, referred to as backset, is recycled back to the front end of the ethanol process as make up water. The remaining thin stillage is evaporated to syrup, added to the wet distiller's grains and dried as Dried Distillers Grains with Solubles (DDGS). WDG, DDG, and DDGS are important co-products that are critical to the economic viability of the ethanol process. However, their value can be enhanced by extracting more valuable co-products from these streams. It has only recently been a goal to recover additional materials from the co-products for further use.

Materials, such as oil, protein, and other solubles in the whole stillage are very valuable; however, recovery has shown to be inefficient and uneconomical. Recently, various methods have been attempted to recover the additional materials from stillage. These methods include traditional separation techniques such as heating the stillage stream and performing evaporation, using centrifugation, or using membrane filtration, in order to recover these additional materials. The result of each of these separation processes on stillage is a concentrate and a water phase wherein most of the solids have been removed.

A number of methods have been developed involving heat treated stillage for the recovery of fermentation by-products, especially oil. U.S. Patent Application Publication No. 2009/0250412 and U.S. Pat. No. 7,608,729 to Winsness, et al. disclose methods for recovering oil from stillage concentrate including oil resulting from a process used for producing ethanol from corn. Winsness, et al. generally believe that filtration increases operating costs and therefore focus on separation by heating. In one embodiment, the method includes heating the stillage concentrate to a temperature sufficient to at least partially separate, or unbind the oil. The heating step includes heating to a temperature above 212 degrees F. but less than about 250 degrees F. The method also includes the step of pressurizing the heated stillage concentrate to prevent boiling. The method further includes recovering the oil from the treated stillage concentrate using a gravity separation process including centrifugation. The process disclosed by Winsness, et al. does not include treatment of unconcentrated stillage streams. While oil can be recovered from the method of Winsness, et al., there are many products in the thin stillage that are not recovered. For example, the process disclosed by Winsness et al. does not include recovery of a high solids-high protein fraction and a stickwater fraction (as defined below) nor the improved fermentative value and alternative uses of stickwater. Furthermore, it is generally accepted in the art that heating the thin stillage to higher than 250 degrees F. is harmful to proteins and other biological components.

U.S. Pat. No. 6,106,673 to Walker discloses a process and system for the separation of a fermentation process byproduct into its constituent components and for the subsequent recovery of those constituent components. The process requires 1) mixing a starting mixture containing ethanol byproducts with a liquid (water) to form a diluted mixture, 2) heating of the diluted mixture containing the byproducts so as to separate the oil from a base component (fiber) of the byproduct to which the oil is bound at a temperature from about 140 degrees F. to about 250 degrees F., followed by 3) recovering oil, the base product (fiber), and possibly other substances such as molasses from the mixture. The process can be performed on a large scale and in a continuous fashion using a mechanical separator to recover fibers from the diluted heated mixture to produce a solids stream and a liquor stream and by then removing oil and insoluble substances from the liquor stream in an evaporator assembly. Energy consumption and water consumption are minimized through 1) the use of waste heat from the system's dryer as an energy source for the evaporator assembly and 2) the use of condensed liquids from the evaporator assembly to dilute the mixture. There is no disclosure in Walker '673 of recycle of recovered water or stickwater to fermentation or improvement of fermentation rate or yield by recycle of any or the entire liquor stream to upstream operations.

Thus, while heating and mechanical separation described in prior art provides some separation of co-products, especially oil, it was not recognized that the use of all or a portion of hydrothermally treated stillage or stickwater can improve fermentation processes.

Thermal hydrolysis has been investigated as a pretreatment step prior to anaerobic digestion of biomass, in particular the anaerobic digestion of waste activated sludge from biological waste water treatment facilities and the pretreatment of cellulosic biomass prior to enzymatic hydrolysis to liberate cellulosic sugars. The former has been commercially implemented while the latter remains a research and development endeavor. Camacho, et al. (Proceedings of the WEFTEC® 2008 Conference, Chicago, Ill. Water Environment Federation) reviewed the use of thermal hydrolysis as a pretreatment to anaerobic digestion of activated sludge and noted the improvements in both sludge dewaterability and biogas yield during anaerobic digestion. Optimal treatment temperatures were generally in the range of 150-200° C. (302-392° F.).

Yu, et al. (Energy & Fuels 2008, 22, 46-60) reviewed the use of hot compressed water (HCW) as a pretreatment for biomass in the production of cellulosic biofuels. The authors focused on the unique physicochemical properties of HCW and the chemistries imparted by HCW as well as the yield of fermentable sugars resulting from enzymatic hydrolysis of the pretreated biomass.

Kim, et al. (including Ladisch) (Bioresource Technology 2008, 99, 5206-5215.) investigated the thermal hydrolysis of distiller's dry grains and solubles (DDGS) from a dry grind ethanol facility as a cellulosic pretreatment prior to enzymatic hydrolysis of the cellulosic biomass. The objective of the thermal treatment of Kim, et al. was to prepare the cellulose of DDGS for downstream enzymatic hydrolysis to glucose by cellulase and beta-glucosidase enzymes. U.S. Pat. No. 5,846,787 to Ladisch, et al. discloses use of thermal hydrolysis in the range of 160-220 degrees C. (320-428 degrees F.) as a pretreatment for cellulosic biomass prior to enzymatic treatment with cellulase.

Other efforts have involved heat treatment and filtration of depleted lignocelluosic fermentation hydrolysate broth to separate undissolved solids from the liquid phase and create a low solids liquid (Hennessey, et al., U.S. Patent Application Publication No. 2012/0178976 and Hennessey, et al., U.S. Patent Application Publication No. 2012/0102823, assigned to Dupont).

It is recognized that the temperatures utilized for hydrothermal pretreatment of biomass prior to cellulosic ethanol fermentation and municipal waste prior to anaerobic digestion are greater (300 degrees F.-450 degrees F.) than those preferred for treating stillage in the present invention (220 degrees F.-300 degrees F.).

Stillage has been investigated for enhancing biological processes. For example, in the prior art ethanol process of FIG. 1, stillage is recycled to the front end as make-up water in the slurry and is referred to as "backset". The proteins and nutrients in the stillage have been recognized as aiding fermentation; however, this benefit is marginal and the suspended solids in backset limit the amount of fresh grain solids that can be added to fermentation. Therefore, there is a need for treating stillage to increase its value in fermentation and other biological processes.

A number of biological and non-biological methods have been developed for the improvement of thin stillage. Jacob P. Tewalt, et al. in WO2012/122393 assigned to POET Research Inc. disclose a method to clarify thin or whole stillage by growing fungi. Wicking, et al. in U.S. Patent Application Publication No. 2012/2094981 assigned to North American Protein Inc. disclose the use of fungi to remove inhibitory compounds from stillage and create a treated backset having improved ethanol fermentation performance.

J. Van Leeuwen, et al in U.S. Patent Application Publication No. 2010/0196994 assigned to Iowa State University disclose a method of continuous fungi cultivation on thin stillage to produce useful products and remediated water with significantly reduced COD (chemical oxygen demand).

M. Reaney, et al. in U.S. Patent Application Publication No. 2011/0130586, assigned to the University of Saskatchewan, disclose a method of recovering a recyclable water from thin stillage or dewatered (concentrated) thin stillage by polar solvent and/or oil extraction of microbial inhibiting metabolites such as glycerol, lactic acid and 2-phenylethanol (PEA) and the phospholipid α-glycerylphosphorylcholine (GPC) which has potential value in pharmaceutical applications.

J. Jump, et al. in U.S. Pat. No. 7,641,928, assigned to Novozymes North America Inc., disclose the use of enzymes to treat stillage and improve the dewatering properties of stillage.

Prior art processes have tried to remove suspended solids from thin stillage with various flocculating, coagulating or precipitating additives and chemical agents. J. Hughes, et al., in U.S. Pat. No. 8,067,193, assigned to Ciba Specialty Chemicals, discloses the use of anionic polymer additives to increase coagulation and precipitation. D. W. Scheimann and A. S. Kowalski in U.S. Patent Application Publication No. 2006/0006116 assigned to Nalco Company, disclose methods of coagulating and flocculating thin stillage suspended solids using anionic polymer flocculants, cationic coagulants and microparticulate settling aids and removing said suspended solids from the thin stillage. J. Collins, et al. in U.S. Patent Application Publication No. 2012/125859, also assigned to Nalco Co., disclose a method involving ionic flocculants for conditioning and processing whole or thin stillage to aid in the separation and recovery of protein and oil fractions. C. Griffiths in U.S. Patent Application Publication No. 2007/0036881 assigned to Ciba Specialty Chemicals, discloses the removal of suspended solids from thin stillage by treatment with polyacrylamide and electrocoagulation. Verkade, et. al. in U.S. Patent Application Publication No. 2009/0110772 assigned to Iowa State University, describe separating solids from a processed broth through chemical reaction with a phosphorous oxoacid to increase the water solubility of insoluble cellulosic, melaninic, ligninic, or chitinic solids.

Various filtration, microfiltration and ultrafiltration processes have been disclosed in the prior art. Bento, et al. in U.S. Pat. No. 5,250,182 assigned to Zenon Environmental Inc., disclose a step-wise membrane separation process to recover lactic acid and glycerol together, from thin stillage in an ethanol stream. The stepwise process consists of ultrafiltration (UF), nanofiltration (NF) and reverse osmosis membrane units. Demineralized water may be recycled to fermentation or to boiler water make-up feed. Bento et al. suggest that the use of the membrane separation process in the production of ethanol based on the dry-milling of corn, substantially reduces or eliminates the use of a conventional evaporator Other prior art processes have described removal of solids from the clarified aqueous phase through the use of filters after separation of hot (140-212 degrees F.) concentrated thin stillage into a light oil phase and a heavy aqueous phase and treating the oil phase with alkali chemicals including spent clean in place (CIP) solutions (Woods, et al., U.S. Patent Application Publication No. 2011/0275845, assigned to Primafuel).

None of these biological and non-biological prior art methods for treatment of stillage and solid-liquid separation (with or without benefit of additives) has been shown to improve fermentation by the surprisingly simple process of hydrothermally treating stillage and utilizing the treated stillage as a media component in a fermentation process.

Various methods have been proposed for utilizing stillage for biological purposes other than ethanol fermentation. M. Kriesler and D. Winsness in U.S. Patent Application Publication No. 2010/0028484 assigned to GS Cleantech, disclose methods for producing lipids from various stillage streams by the yeast *Rhodotorula glutinis*. Kriesler and Winsness also disclose conditioning of the stillage feed stocks by various pre-treatment methods including steam explosion, autohydrolysis, ammonia fiber explosion, acid hydrolysis, sonication and combinations thereof prior to inoculation with the lipid producing micro-organism.

M. Ringpfeil in U.S. Pat. No. 5,981,233 assigned to Roche Vitamins Inc. discloses a process for manufacturing a xylanase enzyme complex from pre-treated thin stillage of rye, where the pretreatment includes removing solids from the rye thin stillage, evaporation of water, adding other nutrient components and autoclaving prior to culturing the enzyme producing organism (Trichoderma).

In summary of the prior art, methods for improving ethanol fermentation, fermentation of other products, or growth of non-alcohol producing microorganisms by addition of stillage which has been hydrothermally treated in the preferred range of 220 degrees F.-300 degrees F. of the present invention has not been described in patents or literature. It has been discovered for the first time that hydrothermally treating stillage and adding the treated stillage to a fermentation process increases fermentation rates and titers. Therefore, it is shown herein that the present invention provides a simple method for improving fermentation by the addition of hydrothermally treated stillage.

While heating and filtration described in prior art provides some separation of co-products, recovery is limited and costs remain high. One advantage of the present invention is that hydrothermal fractionation of stillage produces a physicochemical alteration, which enables a facile separation allowing for improved recovery of co-products. With respect to the present invention, "hydrothermal fractionation" means heating a substantially aqueous stillage stream to a temperature within a prescribed temperature range, and holding at temperature for a period of time within a prescribed residence time range. A saturation pressure is established and maintained during the hydrothermal fractionation step. Physicochemical alteration means that both physical and chemical changes are imparted to the stillage by the hydrothermal fractionation step. Manifest physical changes include changes in the rate of phase separation, relative phase volumetric fractions and phase densities, phase hydrophobicity and changes in color or appearance. Chemical changes include changes in the distribution of non-soluble protein, fat (oil) and carbohydrate (fiber) between the substantially liquid phase and the substantially solids phase. Other chemical changes include solubilization and/or hydrolysis of components to increase the levels bio-available protein and ammonia in the soluble phase. These physical and chemical changes are mutually dependent and hence the term physicochemical is applied.

Thus heating of stillage has been performed as described in the prior art for recovery of corn oil and other by-products; however, it was not recognized that the hydrothermal treatment of stillage according to the present invention imparts physicochemical changes enabling facile separation into a low solids stickwater fraction, oil and high protein solids fraction. Furthermore and importantly, it will be shown herein that the low solids stickwater fraction provides an enhanced nutrient medium for ethanol and other fermentation processes, thus providing an economic advantage.

Therefore, there is a need for a simple method of producing a physicochemical alteration that changes the co-products in stillage and enables facile separation of co-products in ethanol processing as well as providing streams suitable for improving biological production and recovery of valuable co-products, extracts, metabolites and treated water.

SUMMARY OF THE INVENTION

The present invention provides for a method of hydrothermally treating stillage by heating stillage to 200 degrees F. to 350 degrees F., altering physicochemical properties of the stillage, enabling facile separation of the stillage, and creating unique product fractions.

The present invention further provides for a method of performing ethanol fermentation by treating stillage to enable facile separation by heating the stillage to a temperature of 200 degrees F. to 350 degrees F., and separating the treated stillage to recover a high protein solids fraction, a stickwater fraction, and an oil fraction.

The present invention provides for a method of performing ethanol fermentation by separating whole stillage into stillage and wet cake, hydrothermally fractionating the stillage to create unique product fractions by heating the stillage to a temperature of 200 degrees F. to 350 degrees F., separating the heat treated stillage into a high protein solids fraction, a first stickwater fraction, and a stickwater/oil emulsion, recovering oil from the stickwater/oil emulsion, recovering a second stickwater fraction from the stickwater/oil emulsion and adding the second stickwater fraction to the first stickwater fraction, and further processing the first and second stickwater fractions by a process selected from the group including recycling at least a portion of the stickwater to a front end of an ethanol plant, biological processing and chemical processing, and using the first and second stickwater fractions as growth media in the processing step.

The present invention provides for a method of improving fermentation by heating stillage to a temperature of 200 degrees F. to 350 degrees F. resulting in hydrothermally treated stillage, using all or a portion of the hydrothermally treated stillage as a component of a media, and using the media for a process including fermentation and biomass production.

The present invention also provides for a method of performing ethanol fermentation by separating whole stillage into wet cake and stillage, hydrothermally treating stillage by heating the stillage to a temperature of 200 degrees F. to 350 degrees F., and adding all or a portion of the treated stillage to the ethanol fermentation step or an operation upstream of fermentation.

The present invention provides for a method of performing ethanol fermentation by separating whole stillage into a first cut solids stream and thin stillage, performing a particle size reduction step on all or a portion of the first cut solids, returning the reduced particle size solids to the thin stillage stream to produce thick stillage, hydrothermally treating the thick stillage by heating to a temperature of 200 degrees F. to 350 degrees F., and adding all or a portion of the treated stillage to the ethanol fermentation step or an operation upstream of fermentation.

The present invention further provides for a method of increasing bioavailability of stillage components to microorganisms by hydrothermally treating stillage by heating the stillage to a temperature of 200 degrees F. to 350 degrees F., increasing the bioavailability of components in the stillage, and adding the hydrothermally treated stillage to media and providing to microorganisms.

The present invention also provides for oil, stickwater, high protein solids fraction, high protein meal, metabolites, biomass, and media obtained from the methods above.

DESCRIPTION OF THE DRAWINGS

Other advantages of the present invention are readily appreciated as the same becomes better understood by reference to the following detailed description when considered in connection with the accompanying drawings wherein:

FIGS. 10A-10D are graphs of ammonia, soluble (BCA) protein, crude fat and change in suspended solids vs. thin stillage plotted against the reaction severity factor for the designed experiment of Example 4;

DETAILED DESCRIPTION OF THE INVENTION

Figure 1:
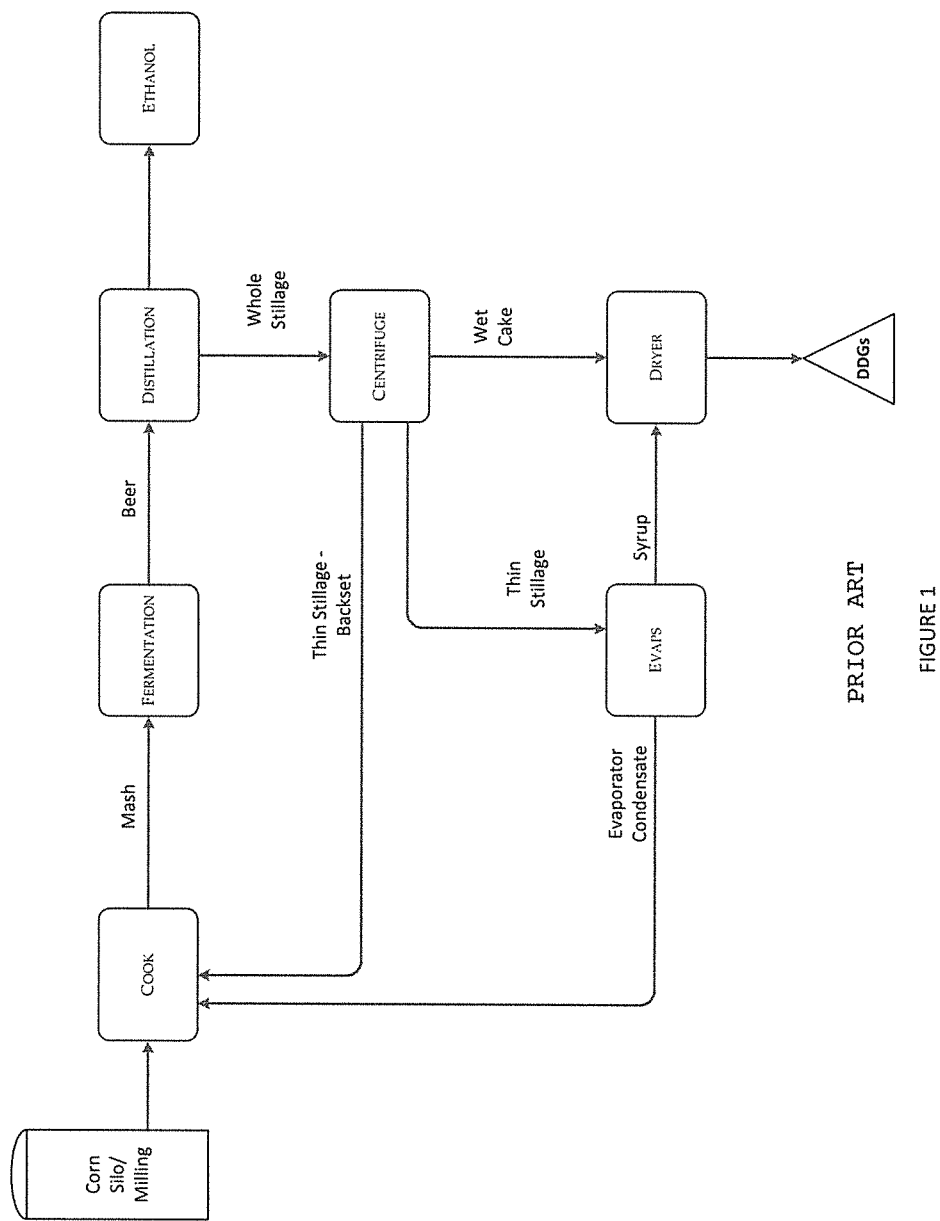
FIG. 1 is a flowchart of a prior art ethanol fermentation process.

Most generally, the present invention provides for methods of ethanol fermentation that include processing of stillage to improve the overall fermentation process and generate useful products. The present invention provides a method of hydrothermally treating stillage by heating stillage to a temperature of 200 degrees F. to 350 degrees F., altering the physicochemical properties of the stillage, enabling facile separation of the stillage and creating unique product fractions. Preferably, these product fractions include a fraction high in oil, a high protein solids fraction, and a stickwater fraction having low amounts of oil and suspended solids. In addition to low suspended solids and oil content, the stickwater fraction is chemically different than thin stillage of the prior art and can serve as improved backset in an ethanol process and as an improved fermentation medium for other fermentation processes.

"Stillage" as used herein, refers to a cloudy liquid produced during ethanol fermentation that includes solids that are not fermentable, solubles, oils, organic acids, salts, proteins, and various other components. As described in the Background Art, in conventional dry-grind corn ethanol operations the effluent stillage from the bottom of the beer column is known as "whole stillage" which is then separated by centrifugation into "wet cake" and "thin stillage". In the current ethanol production process, the suspended solids in thin stillage limit the effectiveness of the evaporators and decrease the efficiency of the fermentation process.

"Stickwater" as used herein, refers to a fraction of the stillage stream that is generally very low in suspended solids, typically less than 1 wt % or less than 50% of the suspended solids in conventional thin stillage, and is mainly water and solubles. This term is also further described below.

"High protein solids" as used herein, refers to a fraction of the hydrothermally treated stillage stream that contains greater than 30 wt % of protein on a dry weight basis.

The term "fermentation" as used herein, refers to a biological process, either anaerobic or aerobic, in which suspended or immobilized micro-organisms or cultured cells in a suitable media are used to produce metabolites and/or new biomass.

In the prior art, thin stillage is either evaporated and added to dried distiller grains or recycled as backset to the front end of the process. The suspended solids in the portion of the thin stillage that is evaporated cause fouling. The evaporators must be oversized to account for this fouling. The evaporators must be taken off-line from time to time for cleaning. This adds to the capital cost and operating cost of an ethanol plant.

Thin stillage used as backset is less than ideal for that purpose. The suspended solids present in backset limits the amount of corn that can be added during the slurry process. Because of the non-fermentable solids in the backset, pumps, heat exchangers, and fermenters must be oversized, increasing the capital cost and operating cost of the process. Furthermore, the suspended solids in the stillage can interfere with the utilization of nutrients during fermentation.

Thin stillage used as backset is also less than ideal because the thin stillage contains glycerol, organic acids and other yeast metabolites. These compounds act as fermentation inhibitors, slowing fermentation and decreasing throughput.

Using thin stillage as backset does have some advantages. The soluble proteins from the corn and dead yeast cells act as nutrients; however, insoluble proteins cannot be utilized. Ethanol plants will operate the stillage centrifuge to maximize overall plant efficiencies which results in thin stillage typically in the range of 1.5%-3% suspended solids (4%-6% total solids). Preferably, when thin stillage is used herein, it has 4% or less suspended solids. However, the stillage processing method of the present invention creates low solids stickwater that avoids the operational issues associated with higher solids.

In the present invention, processing stillage with higher suspended solids than thin stillage of the conventional process has advantages. It is known that oil is bound to the suspended solids in stillage. By manipulating the solids content of stillage, the present invention can produce a desired protein and oil yield. Processing stillage with higher solids content can also produce a stickwater that is more suitable for use as a fermentation media, increasing ethanol titer. Therefore, the stillage that is processed in the method herein can be whole stillage, containing approximately 8-10% suspended solids (11-13% total solids) or a stillage where the total suspended solids are reduced to a level below whole stillage, including reducing solids to the level of thin stillage. Stillage with a suspended solid content less than whole stillage and more than thin stillage is referred to as thick stillage. Thick stillage can have approximately 3 to 8% suspended solids, and preferably between 4 to 8% suspended solids. The solids separation can be done in one or more steps.

In the method of ethanol fermentation, the corn is milled, slurried, and cooked with enzymes to obtain a sugar-rich mash, fermented to obtain a beer, distilled to produce ethanol, and centrifuged to obtain stillage as shown in FIG. 1. Then, once stillage has been produced, the stillage processing method of the present invention can be introduced into the fermentation process at different points in order to obtain certain products, as further detailed below.

The stillage used in any of the methods herein can be whole stillage, diluted stillage, thin stillage, thick stillage, or concentrated stillage. Diluted stillage can include a diluting liquid such as, but not limited to, water, process water, steam, or process vapor (such as, but not limited to, flash steam, distillation vapor, distillation vapor condensate, evaporated thin stillage vapor, evaporated thin stillage vapor condensate, evaporated stickwater vapor, evaporated stickwater vapor condensate, dryer vapor, or dryer vapor condensate).

Thick stillage can be produced by methods such as removal of water from stillage to concentrate solids, filtration of stillage, centrifugation of whole stillage under centrifuge operating conditions promoting transport of more solids into the centrate, addition of solids to thin stillage, particle size reduction of stillage to increase the suspended solids in the feed to hydrothermal treatment, particle size reduction of grain or a grain slurry to increase the suspended solids in the feed to hydrothermal treatment, and combinations thereof.

Thin stillage can be used in the processing method described in further detail below to generate a stickwater fraction and a high protein solids fraction. Thin stillage is obtained by running the centrifuge in the ethanol fermentation process under normal operating conditions.

Those skilled in the art appreciate that there are various methods to create a thick stillage stream. After the distillation process, the largest solids (for example, greater than 100 µm) can be removed or separated from the whole stillage by use of a centrifuge, filter, membrane, flocculating polymers, dissolved air flotation, or any other suitable separation method to generate a "large solid wet cake" and a thick stillage. For example, thick stillage can be obtained by running the centrifuge in the normal ethanol process at reduced speed or for less time than is used to generate thin stillage. By generating a thick stillage by this method, centrifuge operational reliability is enhanced and more oil and other products can be obtained. DDGS are not materially affected with lower productivity as the high protein solids fraction is further separated at high temperature.

Alternatively, thick stillage can also be generated by performing a particle size reduction on all or a portion of the whole stillage stream and combining those reduced particle solids with thin stillage to create thick stillage. Thus the flexibility of the present invention allows for varying solids concentration and stickwater can still be obtained.

Whole stillage can also alternatively be used in the processing method of the present invention and similarly generates a stickwater fraction and a high protein solids fraction. In other words heating the stillage at the temperature described herein, whether whole, thick, or thin, results in a high protein solids fraction and a stickwater fraction with unique properties. The suspended solids content of the stillage can be varied to tailor the desired amount and composition of products in each fraction.

Figure 2:
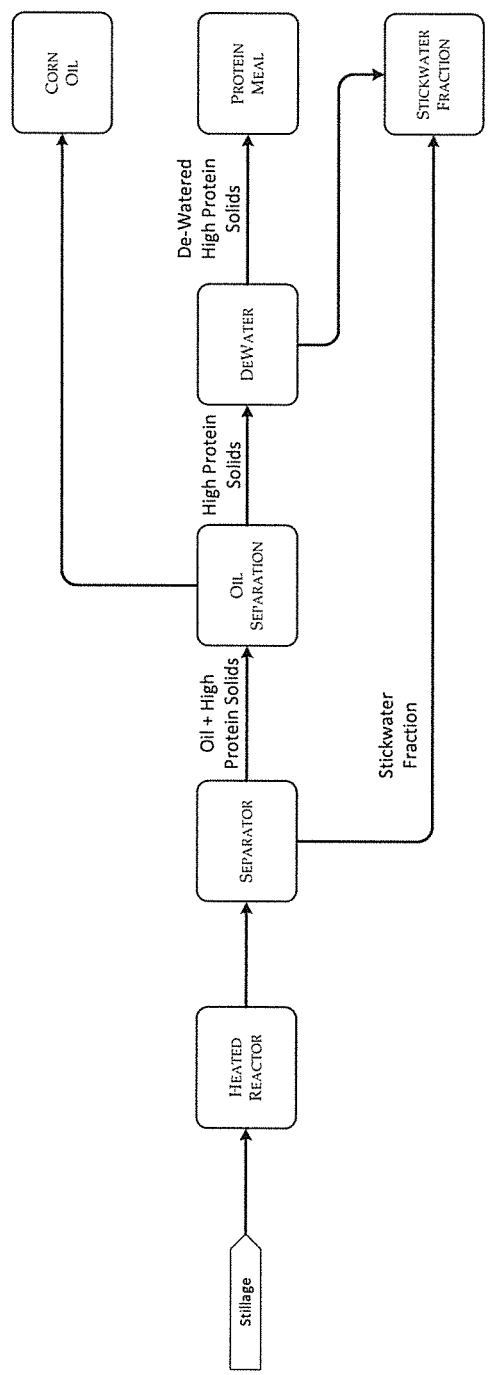
FIG. 2 is a flowchart of the hydrothermal fractionation process of the present invention.

The goal of hydrothermal fractionation is to obtain valuable fractions, reusable water, and improved fermentation media. FIG. 2 shows the main steps of the hydrothermal fractionation method. First, the stillage is heated by a heating mechanism, such as, but not limited to, a heat exchanger or steam injection, to a temperature of 200 degrees F. to 350 degrees F. in a pressurized reactor. More preferably, the stillage is heated to 220 degrees F. to 300 degrees F. Even more preferably, the stillage is heated to 240 degrees F. to 290 degrees F. The reactor pressure is maintained at or above the saturation pressure of the stillage. The stillage is maintained at that temperature for 3 to 180 minutes. Afterwards, preferably, the stillage is cooled below its atmospheric boiling point, and preferably below 212 degrees F.

The hydrothermal fractionation step essentially "conditions" the stillage to enable facile separation and creates unique product fractions. These altered fractions cannot be obtained in the prior art processes. Unexpectedly, the stillage can readily separate even under quiescent settling conditions into a high protein solids fraction containing oil and protein solids and a stickwater fraction due to this heating step. The physicochemical change imparted on the stillage by the heating step makes the solids in the stillage less hydrophilic and makes it easier for the stickwater phase to separate from the oil and solids phase. While further mechanical partitioning processes can also be applied as described below, it is unexpected that merely by heating the stillage at this particular temperature range, the stillage can separate into the oil/solids fraction and the stickwater fraction.

As implied by the term physicochemical, the stillage also undergoes chemical changes. Stillage is a complex mixture of yeast cells, proteins, fiber, lipids, minerals, salts, organic acids, glycerol, monosaccharides and oligosaccharides. Many of the components of the stillage are useful to microorganisms, but are not bio-available. The process of hydrothermal treatment converts or releases these components to increase their bioavailability.

For example, stillage contains many oligosaccharides, a polymer that cannot be metabolized by many micro-organisms. The hydrothermal treatment of stillage hydrolyzes the oligosaccharides into monosaccharides and disaccharides.

The proteins in stillage are present in tight matrixes. These matrixes bind the proteins, phosphates, sugars, cations, anions, metals, salts and amino acids. The hydrothermal treatment of stillage unfolds the proteins in a way that increases the bioavailability of these components. The hydrothermal treatment of stillage denatures and hydrolyzes proteins, increasing the bioavailability of ammonia and soluble proteins.

Stillage also contains corn oil. Corn oil adheres to microorganism cells retarding their ability to convert carbon into biomass or metabolites. The hydrothermal treatment of stillage reduces the corn oil emulsion in stillage making the oil easier to extract. The extraction of oil from stillage reduces the negative effect corn oil has on fermentation.

In general, the amount of the separation due to the heat itself depends on the degree of solids removal prior to the hydrothermal fractionation step. If stillage with a low suspended solids level is used, the hydrothermal fractionation step readily induces separation. If whole stillage is used, the separation does not happen as readily as with thin stillage and whole stillage can therefore require a further mechanical partitioning or separation step as described below. Thus, in general, the heating step makes it easier to release water from solids in the stillage regardless of the type of stillage used. It should also be understood that the heated stillage can directly be used without separating.

In general, after the enabling step, the stillage is separated into at least one of the high protein solids fractions, a stickwater fraction, and an oil fraction. The mechanical separation can be achieved with a method such as, but not limited to, gravity (quiescent decantation), screens, filtration, membranes, hydrocyclones, centrifugation, decanter centrifugation, three-phase decanter (tricanter), dissolved air flotation, or any other suitable method. For example, the separation can be quiescent decantation for 10 to 180 minutes.

The stillage can be separated into a light phase which is substantially oil and a heavy phase which is substantially stickwater and high-protein solids, and the heavy phase can be separated into a high protein solids phase and a low solids stickwater phase. The separation of the stillage into a light phase can be performed with a series of centrifugal separators. The separation of the heavy phase can be performed with a decanting centrifuge. Alternatively, the stillage can be separated into a light phase containing stickwater and oil and a heavy phase containing substantially the high protein solids fraction, and the light phase can be separated to produce a low solids stickwater fraction and an oil fraction. In this case, the stillage can be separated into the light phase with a decanter and the light phase can be separated by a centrifuge or quiescent decantation. Any emulsion present in the light phase of quiescent decantation can be separated by an additional centrifugation step. The stillage can also be separated by performing quiescent decantation to produce a bottom heavy phase which is substantially the low solids stickwater fraction and a top light phase which is substantially high protein solids and oil. This method can further include the step of separating the top light phase into an oil fraction, a high protein solids fraction, and additional low solids stickwater fraction.

The separation can be performed with a single separation device such as, but not limited to, a three-phase decanting centrifuge ("tricanter"), a three-phase nozzle centrifuge and a three-phase disk stack centrifuge. When a tricanter is used, preferably, the fractions obtained include a high protein solids fraction, a stickwater fraction, and a stickwater/oil emulsion. The stickwater/oil emulsion can be separated to produce an oil fraction and a second stickwater fraction.

The stickwater fraction has a very low suspended solids (oil or other solids) content of less than 1%, and the present invention provides for the stickwater recovered from the methods herein. The stickwater fraction can be recycled to the front end of the plant as enhanced backset to form the corn slurry, it can also be sent to the evaporators, or any other suitable point in the ethanol fermentation process. Since the majority of the solids have been removed from the stickwater fraction used as backset, more corn flour can be added to the slurry as compared to when using thin stillage in the slurry, thereby directly increasing the plant's capacity to produce ethanol, DDGS, and corn oil. That portion of the stickwater which is not recycled as backset but is instead forwarded to the evaporators, results in improved evaporator efficiency and operability (less fouling) due to the reduced suspended solids content of stickwater compared to stillage.

The method can further include recycling as fermentation makeup water at least a portion of the stickwater to a process step upstream of fermentation in ethanol plant (such as grain slurry, liquefaction, cook, enzymatic hydrolysis, sugar washing and sugar concentrating), filtering at least a portion of the stickwater fraction with membranes or other filtering device, dehydrating at least a portion of the stickwater fraction, concentrating at least a portion of the stickwater fraction, removing glycerol, removing organic acids, removing other organic compounds, removing inorganic compounds such as minerals, metals and salts, adding agents to at least a portion of the stickwater fraction to precipitate components, treating at least a portion of the stickwater fraction and removing fermentation inhibitors, and combinations thereof. Any of the products recovered from these methods are also provided.

The preferred end-products of the hydrothermal fractionation process are oil, a low suspended solids stickwater fraction, and a high protein solids fraction. Once the stillage has been hydrothermally treated to induce the physicochemical changes, multiple process schemes can be envisioned for separating the treated stillage into the preferred end products. These schemes differ based on the type of equipment deployed, the residence time, and the relative g-forces imparted by the specific equipment. Separation can be achieved with a method such as, but not limited to, gravity (quiescent decantation), centrifugation, decanter centrifugation, dissolved air flotation, or any other suitable method. For example, the separation can be quiescent decantation for 10 to 180 minutes. Some examples of separation schemes are provided in the accompanying figures and are described below. Those skilled in the art will recognize that other schemes and equipment options can be utilized to arrive at the desired end-products. Furthermore, it is not necessary to perform all separations and intermediate product compositions can be isolated if desired.

Once the first stickwater fraction has been produced by centrifugal decantation or quiescent decantation, the low specific gravity fraction containing oil and high protein solids can be further dewatered or concentrated. The physical properties of the low specific gravity fraction make it suitable to mechanical dewatering with traditional methods (belts, decanters). The de-watered protein/oil fraction can be recovered as a separate product. The low specific gravity fraction containing oil and protein solids can also be concentrated by high speed disk stack centrifugation, dissolved air flotation, evaporation, or any other suitable method. Oil can be weight separated from the protein fraction. The de-oiled high protein stream resulting from the removal of oil can be recovered as a separate product. The dewatered high protein solids can be further processed in evaporators or dryers. Water recovered from dewatering the high protein solids fraction can either be combined with the first stickwater fraction stream or kept as a separate stream. The dewatered protein fraction represents a small portion of the total stillage flow, typically 5%-10%, but the high protein content make it valuable. The dewatered de-oiled protein fraction is preferably over 20% solids w/w and more preferably over 25% solids w/w. Alternatively, the oil recovery and dewatering step can be combined into a single step using a three-phase decanter or other suitable methods.

Figure 3:
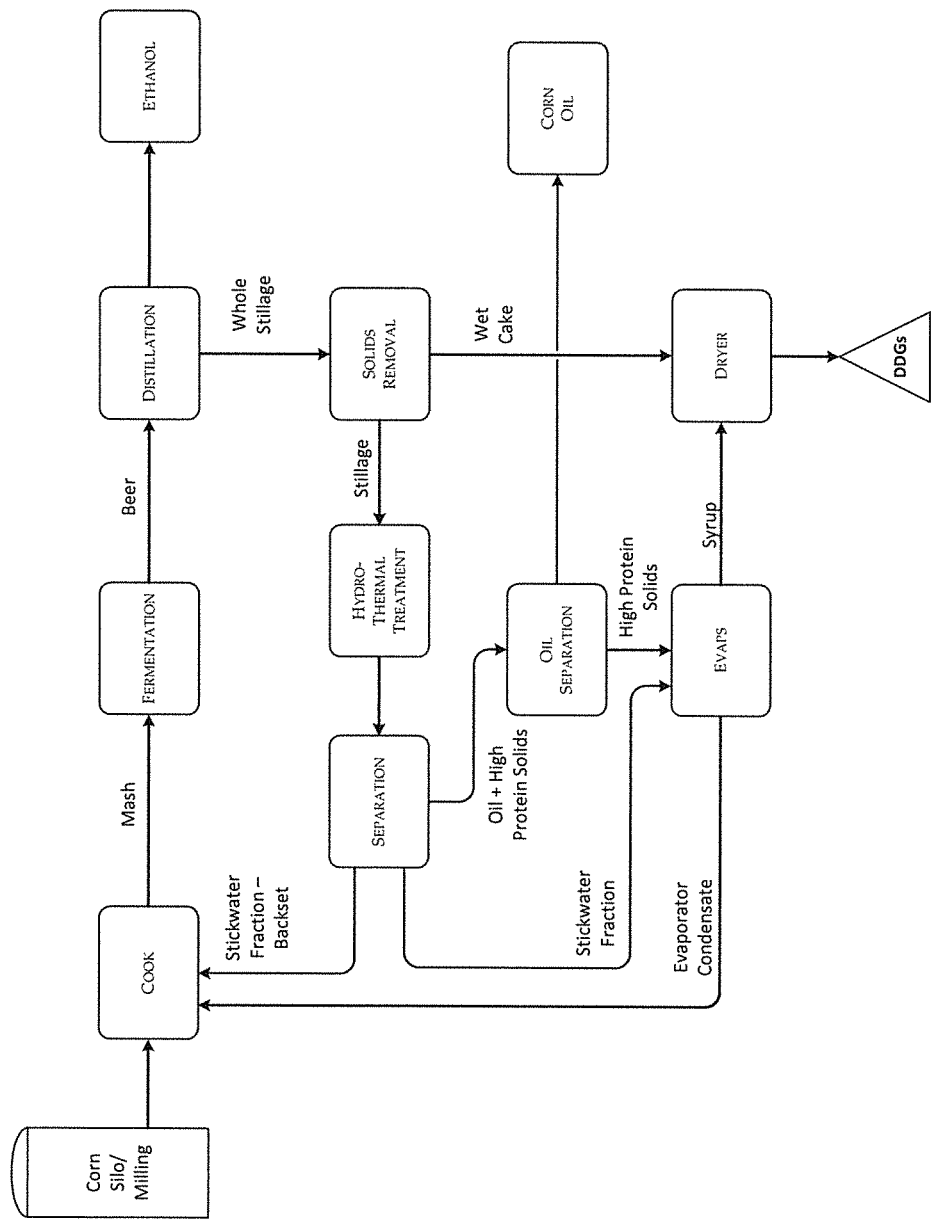
FIG. 3 is a flowchart of the hydrothermal fractionation process of the present invention added after separating whole stillage into stillage and wet cake, followed by stickwater separation and then oil separation from the high protein solids fraction, stickwater not recycled as backset and the high protein solids fraction are processed through the evaporators and recovered in DDGS.

One processing option and separation scheme is shown in FIG. 3. Large solids can be removed from the stillage, if desired. The stillage is hydrothermally fractionated then separated for example by quiescent decantation into a relatively higher specific gravity bottom layer comprising stickwater and a relatively lower specific gravity top layer comprising high protein solids and oil. Oil (such as corn oil) can be removed from the low specific gravity fraction, by for example a centrifugal decanter, and the oil and protein fractions are thereby recovered. Stickwater can be sent to the cook step at the front end of the process as enhanced backset. Some or all of the stickwater and protein fractions can be sent to the evaporators, and separated into the evaporator condensate that is sent back to the cook step, and the concentrated, protein fraction that is sent to the dryer as syrup to add to the DDGS.

Therefore, the present invention also provides for a method of performing ethanol fermentation, including the steps of separating whole stillage into stillage and wet cake, performing the method of hydrothermal fractionation as described above, recovering a stickwater fraction, a protein fraction and oil, and recycling some or all of the stickwater to the cook step as enhanced backset. The method can further include the steps of evaporating the stickwater fraction and the protein fraction, recovering evaporator condensate and recycling to the cooking step; and recovering concentrated protein fraction and drying the concentrated protein fraction and obtaining dried distillers grains.

Figure 4:
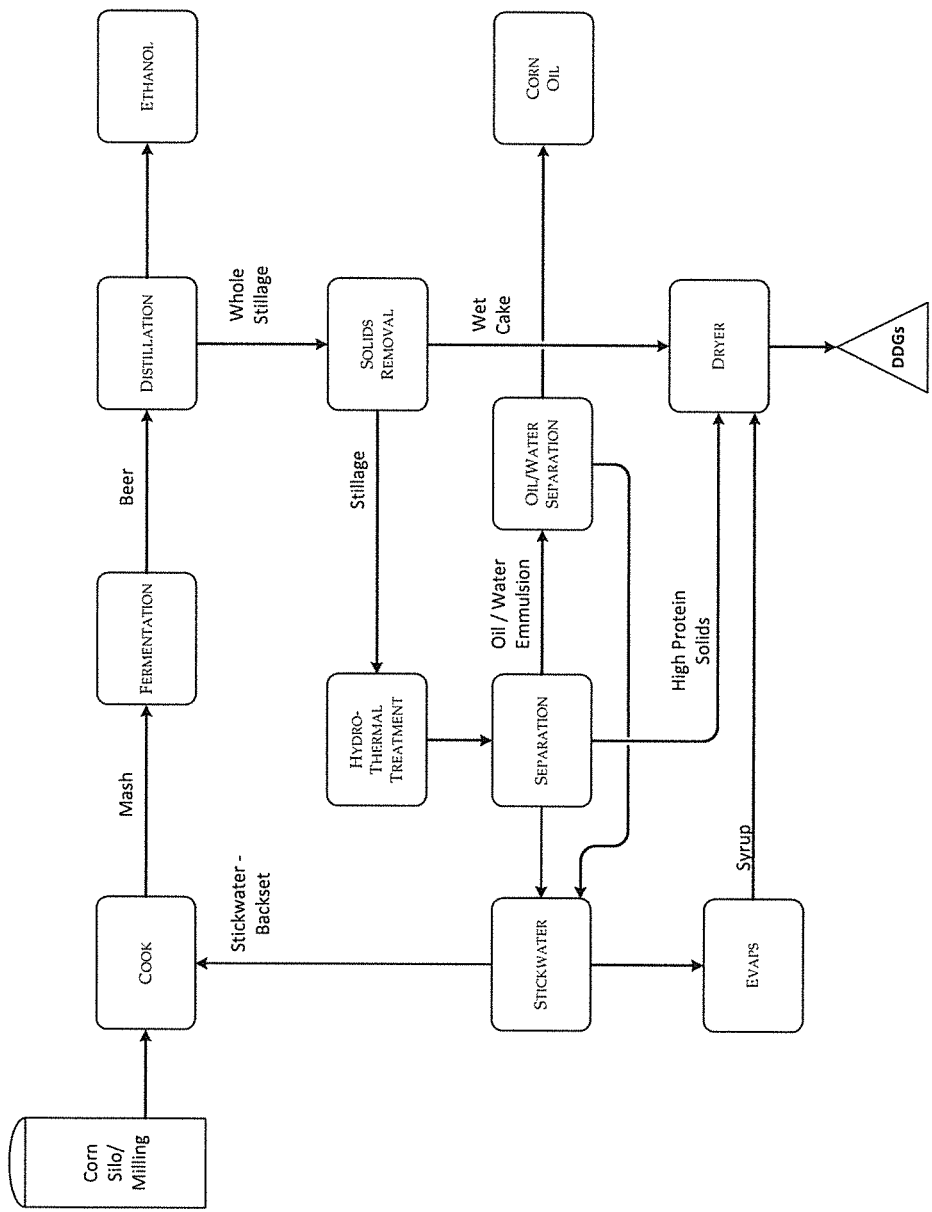
FIG. 4 is a flowchart of the hydrothermal fractionation process including the optional step of separating whole stillage into stillage and wet cake, followed by separation of treated stillage in a three-phase decanter known as a "tricanter" giving an oil-water emulsion, stickwater, and high protein solids fraction, the oil-water emulsion can be centrifugally separated into oil and additional stickwater, and stickwater not recycled as backset and high protein solids fraction are recovered in DDGS.

Another processing option and separation scheme is shown in FIG. 4. Stillage is optionally separated into wet cake and stillage and heated in a pressurized reactor. It is then separated into three streams by a three phase decanter (tricanter) or a three phase centrifuge to give cream, liquid, and solids. The cream is an emulsion of oil and water with a small amount of solids. The tricanter liquid stream is mainly stickwater with dissolved solids and low suspended solids. The tricanter solids are mostly suspended solids of fiber and protein (10%-15% moisture). Oil can be separated from the cream, for example, with a high speed centrifuge. The liquid stream (stickwater) can be recycled as backset, evaporated, or used for some other purpose. The solids can be furthered de-watered and/or dried to form a high protein meal. The present invention provides for the high protein meal obtained and recovered from the methods herein.

Figure 5:
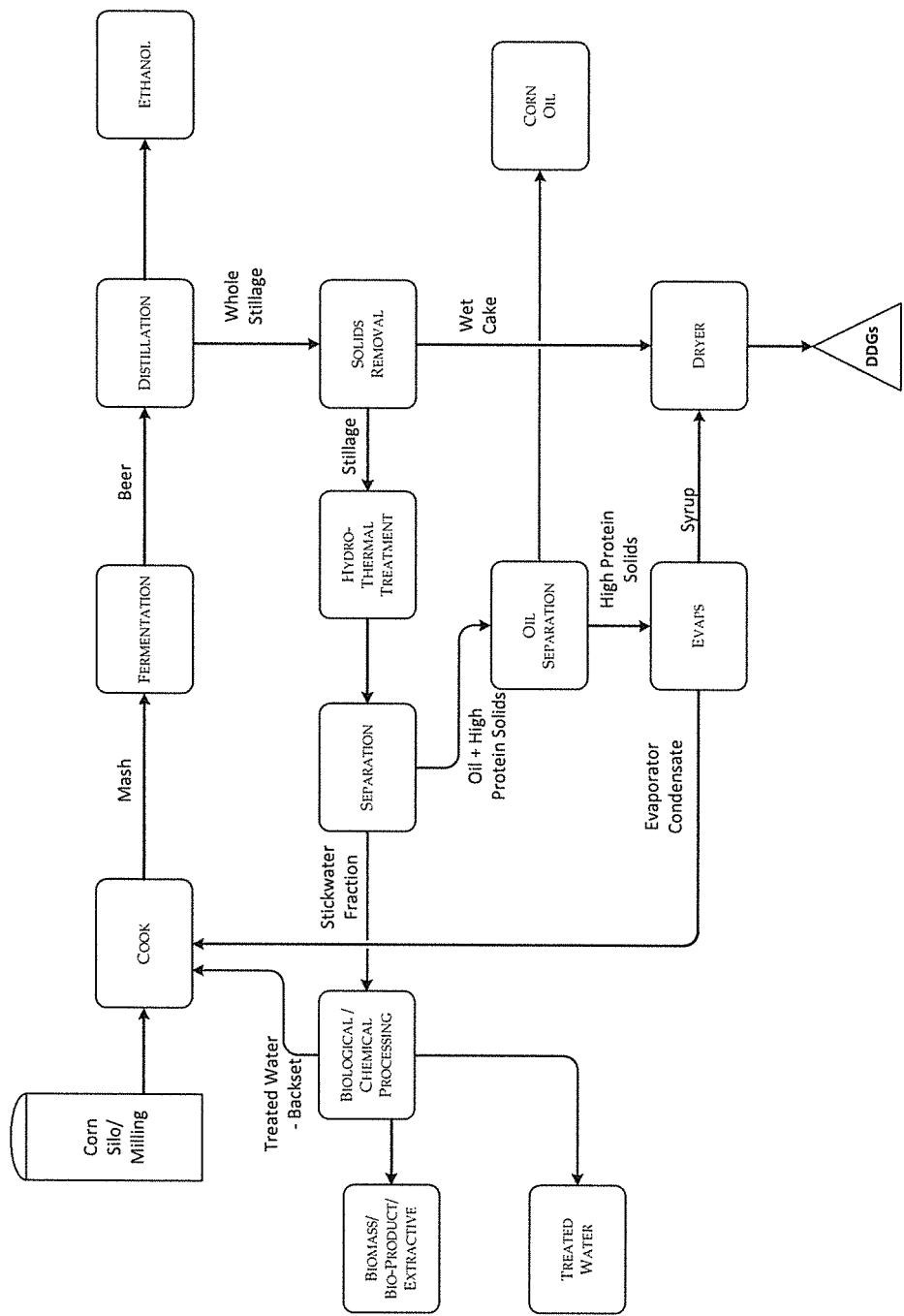
FIG. 5 is a flowchart of the hydrothermal fractionation process of the present invention added after separating whole stillage into stillage and wet cake, followed by hydrothermally fractionation of stillage, separation of stickwater from treated stillage and processing of stickwater by biological and/or chemical processing.

The process shown in FIG. 3 can be further altered so that the stickwater fraction produced by hydrothermal fractionation is sent for further biological or chemical processing as shown in FIG. 5. The stickwater fraction can be treated biologically to further remove fermentation inhibitors. Metabolites that are fermentation inhibitors are still present in the stickwater fraction after separation, but without the suspended solids, they can more easily be removed with standard industrial processes such as anaerobic digestion.

Alternatively, algae, fungi, or any other suitable microorganisms can be added to the stickwater fraction and the stickwater fraction acts as an improved growth media. Components in the stickwater, including ammonia, trace minerals, proteins, and carbohydrates can be used by various microorganisms. Yeast metabolites, such as glycerol and organic acids, can be used as a carbon source by GMO (genetically modified organism) and non-GMO micro-organisms. These micro-organisms can produce biomass, ethanol or other higher value biofuels or bio-based chemicals. For example, a modified *E. coli* or yeast can metabolize glycerol to ethanol. After the biological treatment, the stickwater fraction can be recycled or sold.

The low solids stickwater can be further processed in order to selectively isolate components. The stickwater fraction can be concentrated by evaporation or membrane separation. Membranes can be used to perform ultrafiltration and/or nanofiltration of the stickwater fraction giving a demineralized water stream that is essentially free of dissolved solids and organic compounds larger than membrane pores. Multiple membranes can be used in series. A reverse osmosis (RO) membrane can also be used after the aforementioned filtration steps. Any components isolated by the membranes can be recovered for additional use, such as, but not limited to, lactic acid and glycerol. Additionally, the stickwater can also be chemically treated by addition of acids, bases or other agents to precipitate and recover minerals and salts and/or by addition of solvents to extract metabolites, organic components or plant extractives.

After the biological or chemical processing steps described above, biomass, bio-products, metabolites, and/or extracts can be recovered along with treated water. The treated stickwater can be sold or recycled to the cook step for further use.

Figure 6:
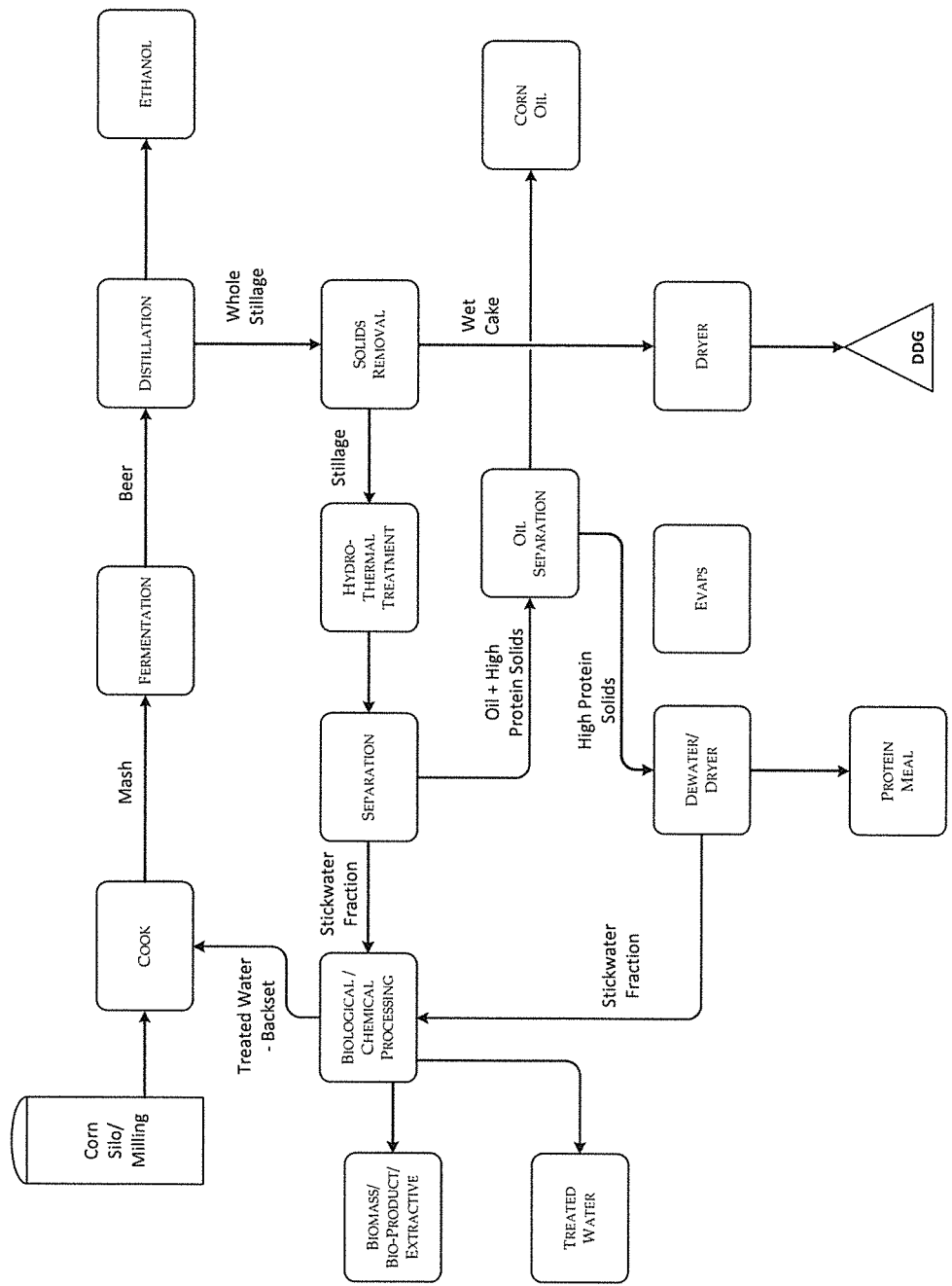
FIG. 6 is a flowchart similar to FIG. 5 including biological and/or chemical processing of stickwater and further including dewatering of the high protein solids fraction to produce dewatered high protein solids to produce protein meal and a second stickwater fraction.

A further process option is shown in FIG. 6, also based on the placement of the hydrothermal fractionation in FIG. 5. In this process, once the protein fraction has been recovered, the protein fraction is dewatered, producing an additional stickwater stream that is sent to the biological or chemical processing step, and a dewatered protein fraction stream that is combined with the wet cake and sent to the dryer to produce dried distillers grains. The treated water from the biological or chemical processing step is recovered and recycled to the front end of the ethanol fermentation process. This process totally eliminates the need for evaporators and reduces cost.

Figure 7:
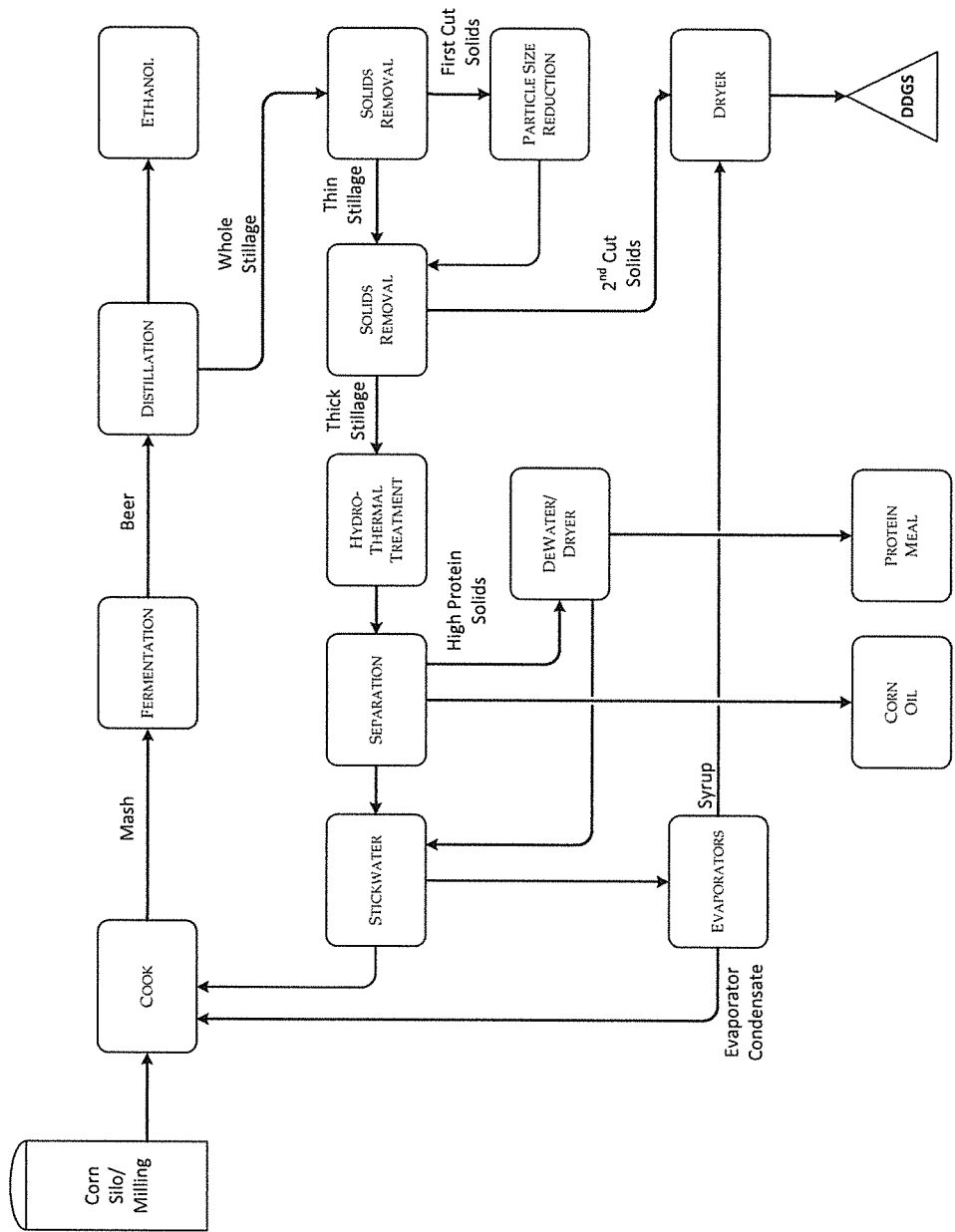
FIG. 7 is a flowchart of the present invention added after separating whole stillage into thin stillage and a first cut solids stream which is forwarded to a particle size reduction step and re-combined with the thin stillage, the combined stream is further separated into second cut solids which are recovered in DDGS and thick stillage which is hydrothermally treated and fractionated into stickwater, oil and high protein solids.

A further process option which exemplifies the use of thick stillage in the present invention is shown in FIG. 7. A solids removal step such as a centrifuge or decanter is applied to whole stillage to obtain thin stillage and a slurry of large particles, denoted as "first cut solids" in FIG. 7. The first cut solids slurry is subjected to a particle size reduction device such as a rotor-stator homogenizer, attrition mill or other such devices known to those skilled in the art. The effluent of the size reduction device can then, for example, be combined with the thin stillage and subjected to a second solids removal step. The fine suspended particles produced in the size reduction step are additive to the suspended particles in thin stillage, thus creating thick stillage. Large particles from the second solids removal step, denoted as "second cut solids" in FIG. 7 are forwarded to a dryer and form the bulk of DDGS solids. The thick stillage from the second solids removal step is hydrothermally treated and separated into stickwater, oil and high protein solids. The dewatered protein fraction can be recovered and dried as a separate product (protein meal) or recovered as DDGS. The use of thick stillage in the present invention provides for additional oil recovery without loss of the enhanced stickwater benefits.

The present invention also provides for a method of performing ethanol fermentation by treating stillage to enable facile separation by heating the stillage to a temperature of 200 degrees F. to 350 degrees F., and separating the treated stillage to recover a high protein solids fraction, a stickwater fraction, and an oil fraction.

This method can further include the step of concentrating the stillage prior to treatment. The method can further include a step such as recycling as fermentation makeup water at least a portion of the stickwater to a process step upstream of fermentation in ethanol plant (such as grain slurry, liquefaction, cook, enzymatic hydrolysis, sugar washing and sugar concentrating), filtering at least a portion of the stickwater fraction with membranes or other filtering device, dehydrating at least a portion of the stickwater fraction, concentrating at least a portion of the stickwater fraction, removing glycerol, removing organic acids, removing other organic compounds, removing inorganic compounds such as minerals, metals and salts, adding agents to at least a portion of the stickwater fraction to precipitate components, treating at least a portion of the stickwater fraction and removing fermentation inhibitors, and combinations thereof. Any of the products recovered from these methods are also provided. The method can further include the step of drying the high protein solids to a high protein meal. The present invention provides for the oil, stickwater, high protein solids, and high protein meal obtained and recovered from this method.

The present invention provides for a method of performing ethanol fermentation by separating whole stillage into stillage and wet cake, hydrothermally fractionating the stillage to create unique product fractions by heating the stillage to a temperature of 200 degrees F. to 350 degrees F., separating the heat treated stillage into a high protein solids fraction, a first stickwater fraction and a stickwater/oil emulsion, recovering oil from the stickwater/oil emulsion, recovering a second stickwater fraction from the stickwater/oil emulsion and adding the second stickwater fraction to the first stickwater fraction, and further processing the first and second stickwater fractions by a process selected from the group consisting of recycling at least a portion of the stickwater to a front end of an ethanol plant, biological processing and chemical processing, and using the first and second stickwater fractions as growth media in said processing step.

The present invention provides for a method of improving fermentation by heating stillage to a temperature of 200 degrees F. to 350 degrees F. resulting in hydrothermally treated stillage, using all or a portion of the hydrothermally treated stillage as a component of a media, and using the media for a process such as fermentation and biomass production.

The heating step is described above and can be further defined as holding the stillage at the temperature for 3 to 180 minutes and at a pressure at or above the saturation pressure of the stillage. The method can further include the step of adding the hydrothermally treated stillage to an operation upstream of a fermentation step. The method can further include the step of cooling the hydrothermally treated stillage prior to use in fermentation media. The fermentation process can produce an alcohol, or a metabolite such as organic acids, alcohols, lipids, carbohydrates, proteins, and secondary metabolites. The fermentation process can be an anaerobic process or an aerobic process. The biomass can be algae, bacteria, yeast, fungi, archae, other microorganisms, or cultured cells. Organic compounds in the hydrothermally treated stillage can provide all or a portion of the carbon source. The hydrothermally treated stillage can provides all or a portion of the nutrient requirements. At least one of a carbon source and nutrients can be added to the media. The carbon source can be dextrose, sucrose, fructose, xylose, arabinose, organic acids, glycerol, ethanol, carbon monoxide, carbon dioxide, methane, other alcohols, other carbohydrates, or other hydrocarbons. The carbon source can be derived from cellulosic material.

The method can further include the step of removing from the hydrothermally treated stillage a composition of suspended solids, dissolved solids, oil, proteins, fiber, or ash. The suspended solids can be removed by a mechanism such as centrifuges, decanting centrifuges, filter centrifuge, filters, membranes, hydrocyclone, quiescent decantation, dissolved air floatation, or flocculation. The dissolved solids can be removed by a mechanism such as membranes, biological remediation, electro-dialysis, ion exchange, distillation, solvent extraction, or precipitation. The method can further include the step of adding one or more agents to assist in the removal of solids such as acids, bases, minerals, polymeric flocculants, microparticulate settling aids (diatomaceous earth, bentonite, montmorillonite, colloidal silica borosilicate, or microsand), precipitation aids, and salts. The temperature can also be adjusted to assist in the removal of solids.

If the stillage is thin stillage, some or all of the solids can be removed from the thin stillage prior to or after the heating step. If the stillage if whole stillage, some or all of the solids can be removed from the whole stillage prior to or after the heating step.

If the stillage is thick stillage, it can be produced by a method such as removal of water from stillage to concentrate solids, filtration of stillage, centrifugation of stillage under centrifuge operating conditions promoting transport of more solids into the centrate, addition of solids to stillage, particle size reduction of stillage increase the suspended solids in the feed to hydrothermal treatment, particle size reduction of grain or a grain slurry to increase the suspended solids in the feed to hydrothermal treatment, and combinations thereof. Some or all of the solids can be removed from the thick stillage prior to or after the heating step.

The method can further include the step of performing size reduction on all or a portion of the stillage (such as thin stillage, whole stillage, wet cake, or thick stillage) prior to or after the heating step. Some of the solids can be removed from the stillage prior to or after the size reduction step. The removed solids can be added back to the stillage after particle size reduction. Solids can be removed from the stillage after the heating step, by a mechanism such as centrifuges, decanting centrifuges, filter centrifuge, filters, membranes, hydrocyclone, quiescent decantation, dissolved air floatation, or flocculation. Size reduction can be performed with a mechanism such as colloid mills (e.g. ball mills, bead mills), disc mills, pin mills, jet mills, rotor-stator mixers, high-pressure homogenizers, and ultra-sonication.

The method can further include the step of removing some or all of the oil from the stillage before or after the heating step. The method can further include the step of separating the metabolites from the fermentation media, and the step of recovering the biomass from the media. The method can further include the step of using fermentation effluent in additional fermentation processes, such as alcohol fermentation. Biomass and/or metabolites can be recovered prior to the additional fermentation process.

The present invention also provides for metabolites, biomass, and media recovered from the above method.

The present invention provides for a method of performing ethanol fermentation by separating whole stillage into wet cake and stillage, hydrothermally treating stillage by heating the stillage to a temperature of 200 degrees F. to 350 degrees F., and adding all or a portion of the treated stillage to the ethanol fermentation step or an operation upstream of fermentation.

The present invention provides for a method of performing ethanol fermentation by separating whole stillage into a first cut solids stream and thin stillage, performing a particle size reduction step on all or a portion of the first cut solids, returning the reduced particle size solids to the thin stillage stream to produce thick stillage, hydrothermally treating the thick stillage by heating to a temperature of 200 degrees F. to 350 degrees F., and adding all or a portion of the treated stillage to the ethanol fermentation step or an operation upstream of fermentation.

The present invention provides for a method of increasing bioavailability of stillage components to microorganisms by hydrothermally treating stillage by heating the stillage to a temperature of 200 degrees F. to 350 degrees F., increasing the bioavailability of components in the stillage, and adding the hydrothermally treated stillage to media and providing to microorganisms. Increasing the bioavailability of components is further defined as a step such as hydrolyzing oligosaccharides into monosaccharides and disaccharides, unfolding protein matrices, denaturing protein, hydrolyzing protein, and combinations thereof.

In summary, there are several key advantages described herein to the various embodiments of the present invention over prior art processes. First, there are components in the stillage that are fermentation enhancers. For example, the proteins from corn and yeast present in the stillage can potentially supply a source of beneficial amino acids and bioavailable nitrogen such as ammonia if properly treated prior to recycle to fermentation. Other insoluble components in the stillage can be fermentation enhancers when solubilized by the present invention. With the stickwater of the present invention, fermentation rates and final titers can be increased.

Second, the present invention allows for the elimination of evaporators. Evaporator condensate that was previously used as make-up water in the cook process can be replaced with additional stickwater. Also, evaporating stillage is energy intensive in prior art processes. Even with the use of multi-effect evaporators, the energy used in evaporation of thin stillage can be as high as 3,000 BTU/gallon of ethanol produced, approximately 10% of all thermal energy used by the plant. Although ethanol plants are highly energy efficient and the energy used in evaporation is recycled to other unit operations, usage minimization or elimination of the evaporators will allow the energy currently utilized for evaporation to be repurposed, such as a Heat Recovery Steam Generator.

Third, the recycled stillage can be detrimental to fermentation in prior art processes. The yeast metabolites produced during fermentation and present in the stillage can act as fermentation inhibitors. Examples are glycerol, lactic acid, and acetic acid, among others. The low suspended solids in the stickwater from the present invention allows for more efficient removal of these inhibitors by application of biological treatment, filtration, or other methods.

Fourth, the suspended solids in the stillage are not fermentable and reduce the amount of new corn flour that can be added to the slurry, as corn ethanol plants typically run at a target total solids target concentration through fermentation to maximize the ethanol produced per bushel of corn processed. By reducing detrimental solids in the backset, hydrothermal fractionation of the present invention can increase ethanol plant efficiency and throughput.

Fifth, stillage, if properly treated is an improved growth media for the production of biomass and bio-products. Thus, one additional use of the stickwater fraction is fermentation media for algae, fungi, and other useful microorganisms. The treated stickwater can be sold as a base media base or aqueous feed along with the other bio-products produced instead of or in addition to being recycled back to fermentation to produce more ethanol.

Sixth, the stillage contains a large portion of corn oil. Corn oil is up to four times more valuable if extracted than if left in the stillage. However, the corn oil is emulsified in the stillage and does not lend itself to extraction easily. Also, it is impractical and expensive to process the entire flow of stillage to extract the oil. With the process of the present invention, the oil can be extracted with a gravity based separation apparatus. Practicing the present invention, between 0.8-1.3 lb corn oil can be recovered per bushel of corn processed into the plant as compared to processes of the prior art where typical yields are 0.4-0.6 lb corn oil per bushel.

Therefore, in summary, the present invention provides for a method of performing ethanol fermentation, including the steps of separating whole stillage into stillage and wet cake, performing the method of hydrothermal fractionation described above, separating and recovering a stickwater fraction, a high protein solids fraction, an oil fraction, and optionally further biologically or chemically processing the stickwater fraction and using stickwater fraction as growth media. The method can also include, before separating the whole stillage into stillage and wet cake, the steps of cooking, fermenting, and distilling corn and obtaining ethanol. The method can include after the further processing step, the steps of recycling some or all of the stickwater to the cook step as enhanced backset, recovering biomass, bio-products, extracts, metabolites, and treated water from the growth media and recycling the treated water. The method can further include drying the protein fraction, or if the dewatering step is utilized, the dewatered protein fraction and recovering a high protein meal. Optionally, the protein fraction, or if a dewatering step is utilized, the dewatered protein fraction can be added to the wet cake, and dried, recovering dried distillers grains.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Analytical Methods Common to Multiple Examples

The following analytical methods, shown in TABLE 1, established by AOAC International, were used throughout multiple examples. Other methods are described within specific examples.

TABLE 1

| Analysis | AOAC Method # |
|---|---|
| Dry Weight or Total Solids (w/w) | 934.01 (24 h, 105 deg C. method) |
| Total Suspended Solids | 934.01 applied to the wet cake of a sample filtered through 2.2 μm filter media. |
| Amino Acid analysis: | 994.12 |
| Neutral Fiber | 962.09E (neutral detergent fiber) |
| Crude Protein | 970.09 (Kjehldahl method) |
| Crude Fat/Oil | 920.39C Ether extraction method) |

Example 1

Analysis and Comparison of Treatment of Thin Stillage by Invention

Procedures

For the present EXAMPLE 1, thin stillage obtained from a commercial ethanol plant was continuously pumped through a series of Plate and Frame Heat Exchangers (PHEs) into a stirred reactor. The PHEs heated the stillage to 285 degrees F. The reactor's pressure was maintained at the saturation pressure of the stillage. The reactor had a mean residence time of 40 minutes. The conditioned stillage was continuously withdrawn from the reactor and cooled to 185 degrees F., then held in a quiescent decantation tank with a mean residence time of 40 minutes. The relatively high specific gravity stickwater fraction was continuously removed from the bottom of the decantation tank while the relatively low specific gravity fraction containing fat and protein was continuously removed from the top of the decantation tank and collected. The volume ratio of stickwater fraction to fat/protein fraction was 1:1.

Methods of Analysis

The AOAC analytical methods listed above were used in this example.

Results and Discussion

TABLE 2 shows a comparison of thin stillage, stickwater and fat/solids fractions.

TABLE 2

|  | Thin Stillage | Fat/Protein Fraction | Stickwater Fraction |
|---|---|---|---|
| Total Solids (w/w) | 8.02 | 8.7 | 6.84 |
| Crude Fat (w/w) | 1.12 | 2.30 | 0.09 |
| Crude Protein (w/w) | 0.99 | 1.18 | 0.65 |

The thin stillage was partitioned into two distinct fractions; a fat/protein fraction and a stickwater fraction. The fat/protein fraction had higher total solids, fat and protein as compared to both thin stillage (8%, 105%, and 19% higher respectively) and stickwater (27%, 2456%, and 82% higher respectively).

Example 2

Analysis and Comparison of Low G Separation of Untreated Thin Stillage and Thin Stillage Treated by Invention Procedures For the present EXAMPLE 2, untreated thin stillage was obtained from a commercial ethanol plant. The untreated thin stillage was collected at approximately 175 degrees F. Treated stillage was prepared by heating collected thin stillage to 280 degrees F. in a stirred 1-gallon batch reactor, held for 40 minutes at temperature, and then cooled to approximately 175 degrees F. One liter containers of treated and untreated stillage at approximately 175 degrees F. were centrifuged at 400×G for 30 seconds. The samples were then divided volumetrically into a top fraction, middle fraction and bottom fraction, each representing ⅓ of the original sample volume.

Methods of Analysis

The AOAC analytical methods listed above were used in this example

Results and Discussion

Figure 8:
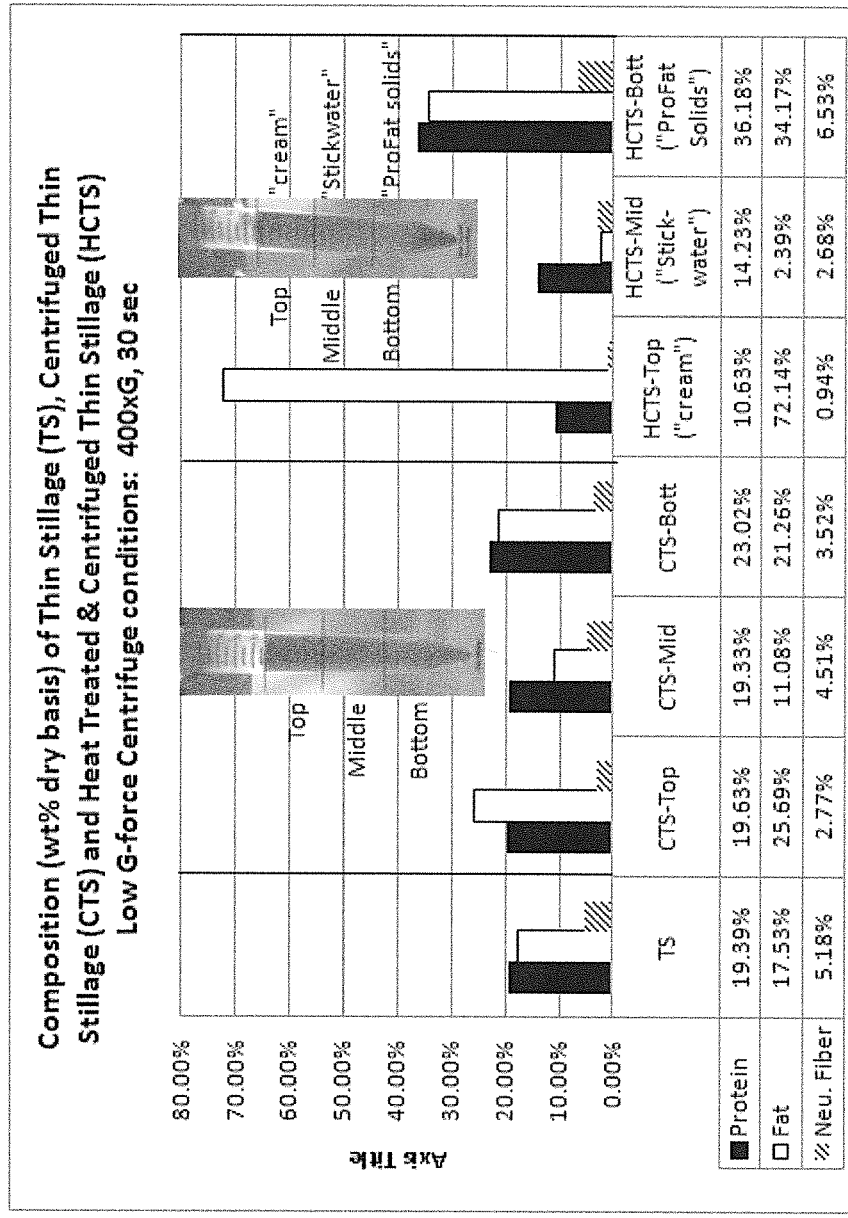
FIG. 8 is a graph showing the composition of untreated thin stillage and hydrothermally fractionated thin stillage after low G-force separation, FIG. 8 also includes photographs of centrifuge tubes to illustrate the facile separation of hydrothermally fractionated stillage under low-g separation.

FIG. 8 shows a compositional comparison of the three fractions from the treated and untreated thin stillage centrifuged in 1 liter containers. The photos in FIG. 8 are of the same samples prepared in 15 mL test tubes which provide a clearer visual depiction (than 1 liter bottles) of the formation of sediment ("Solids") in the treated samples under short duration, low g-force conditions. Sediment was not observed in the untreated sample under low g-force conditions, a further indicator of the facile separation induced by the present invention. The data in FIG. 8 clearly shows that there is no significant partitioning of components top-to-bottom in the untreated centrifuged stillage sample (CTS) while strong partitioning of components occurs in the heat treated and centrifuged thin stillage sample (HCTS) even under low g-force conditions. In particular, the solids fraction is substantially enhanced in fat and protein content relative to thin stillage and the top "cream" portion of the treated sample is likewise enhanced in fat content.

Example 3

Fractionation of Low Specific Gravity Stream from Continuous Decantation and Comparison to Thin Stillage and DDGS Procedures The low specific gravity stream produced as the upper effluent of a quiescent decantation vessel by the method of EXAMPLE 1, was further fractionated by a tricanter into a second stickwater fraction, an oil fraction and a de-watered de-oiled protein fraction. This final protein fraction was analyzed for dry weight total solids, protein, and oil.

The low specific gravity stream produced by the method of EXAMPLE 1 was pumped at a rate of 3 gpm through an Andritz Decanter Model D3L operating at 3000×G. Oil was collected from the skimmer, the second stickwater fraction was collected as the centrate and the de-oiled de-watered protein fraction was collected as the wet cake.

Untreated thin stillage was also collected and pumped at the same rate through the same decanter at the same settings.

The wet material was then dried in a 105 degrees C. oven overnight and then analyzed for dry weight, protein, and oil.

Methods of Analysis

The AOAC analytical methods listed above were used in this example.

Results and Discussion

The dewatered wet cake of the low specific gravity fraction is compared to the wet cake of dewatered thin stillage in TABLE 3. The low specific gravity fraction easily dewatered in the decanter whereas the thin stillage showed virtually no dewatering. This experiment demonstrated the hydrophobic nature and superior dewatering of the solids processed in accordance with this invention.

TABLE 3

Comparison of Wet Cake from Decanter Dewatering

|  | Untreated Thin Stillage | | Treated Low Specific Gravity Stream from Quiescent Settling | |
|---|---|---|---|---|
|  | Decanter Feed | Decanter Wet Cake | Decanter Feed | Decanter Wet Cake |
| Total Solids (% w/w) | 4.9 | 4.9 | 9.1 | 24.2 |

In TABLE 4, the dry weight, protein, fat and neutral fiber analyses for two preparations of the protein fraction (i.e. de-oiled de-watered protein) of the present invention are compared to published data for DDGS. The Protein fraction produced by the present invention has more protein, significantly more fat and significantly less neutral fiber than DDGS.

TABLE 4

Comparison of Protein Fraction to DDGS

|  | Protein Fraction (de-oiled, de-watered) | | DDGS[b] |
|---|---|---|---|
|  | Sample A | Sample B |  |
| Protein[a] | 43.4 | 44.1 | 31.2 |
| Fat[a] | 35.7 | 38.7 | 11.5 |
| Neutral Fiber[a] | 1.0 | 0.9 | 42.3 |
| Other by difference | 19.9 | 16.3 | 15.0 |

[a]Expressed as a % of the dry wt.
[b]Average values from Fastinger and Mahan, (J. Anim. Sci. 84:1722-1728, 2006) and Stein et al. (J. Anim. Sci. 84: 853-860, 2006) as presented in A. A. Pahm's Ph. D thesis U. of ILL, p. 66 Table 2.1, 2008.

This example illustrates the utility of the invention. A corn ethanol plant can recover a new, high value co-product that is significantly different than the current DDGS co-product. Again, due to the facile separation resulting by heating; proteins, fats, and fibers are obtainable in amounts that would otherwise not be possible to obtain by prior art processes.

Example 4

Effect of Time and Temperature on Hydrothermal Fractionation

Procedures

For the present example, a two factor statistical design of experiments (DOE) methodology was used to evaluate the effect of time and temperature on hydrothermal fractionation of thin stillage. The central composite design (CCD) covered the time-temperature ranges of 4-116 minutes and 184 degrees F.-296 degrees F., with a center point at 60 minutes, 240 degrees F. replicated four times. Thin stillage obtained from a commercial ethanol plant was pumped from a well-stirred 5-gallon plastic container through a series of Plate and Frame Heat Exchangers (PHEs) into a stirred 1-gallon batch reactor. The PHEs heated the stillage to the target temperature and the jacketed reactor held the stillage for the prescribed residence time. The reactor pressure was maintained at the saturation pressure of the stillage. At the end of the prescribed residence time, the reactor contents were gravity drained into a clean 1-gallon plastic container, uniformly mixed and poured off into 1-L wide-mouth plastic bottles. The 1-L bottles were centrifuged in a bottle centrifuge (Damon/IEC model EXD centrifuge, Needham Heights, Mass., USA; approx. 18 inch inside chamber diameter) by ramping to full speed (3100 rpm, 2714 G-sec), holding for 1 minute at full speed and ramping down. At the end of centrifugation, the typical top-to-bottom partitioning of material in a full 1-L bottle comprised about 1-2 cm of a floating oil emulsion, about 10 cm of stickwater and about 1-1.5 cm of deposited solids. The oil and water layers from each 1-L bottle were carefully poured off, taking care not to disturb the deposited solids into a 1.25 gallon bench-top gravity decanter (a clear plastic water container of dimensions 12.5 in. length×9 in. height×3 in wide, set on its narrow face at about a 15 degree angle, and equipped with a low point drain valve). The oil and water layers were allowed to gravity separate in the bench-top decanter for 5 minutes after which the bottom stickwater phase was drained through the low-point valve, leaving a small volume of stickwater in the decanter so as to assure a stickwater sample containing no second phase oil. Finally the oil phase was drained from the bench-top decanter with a small amount of residual stickwater. The thin stillage feed and stickwater from each heat treatment condition were analyzed for soluble ammonia, soluble protein, crude protein, crude fat (oil), total solids and suspended solids.

Methods of Analysis

The AOAC analytical methods listed in the table above for crude protein, crude fat, total and suspended solids were used in this example. Specific methods for soluble ammonia and soluble protein are given below.

Soluble protein was analyzed according to the "BCA" method of Smith et al. (Smith, P. K., et al. (1985). Measurement of protein using bicinchoninic acid. *Anal Biochem* 150: 76-85.)

For ammonium determination, the indophenol method according to M. Krom (*Analyst* 105, 1980, 305-316), a modified Berthelot reaction, was miniaturized as described by C. Laskov et al. (*Limnol. Oceanogr.: Methods* 4, 2007, 63-71) The reagents were prepared as follows. (A) Buffer solution: In a 1000-mL flask, 33 g potassium sodium tartrate ($C_4H_4O_6KNe4*H_2O$) was dissolved in 500 mL, then 24 g sodium citrate ($C_6H_5O_7Na_3*2H_2O$; complexing agent) was added and diluted to 1000 mL. The pH should be controlled and if necessary conditioned to 5.2 by addition of hydrochloric acid. (B) Sodium salicylate solution (phenolic component): 25 g sodium hydroxide (NaOH) was dissolved in 500 mL, then 80 g sodium salicylate ($C_7H_5NaO_3$) was added and the mixture diluted to 1000 mL. (C) Sodium nitroprusside solution (catalyst): 1 g sodium nitroprusside ($Na_2[Fe(CH)_5NO]*2H_2O$) was dissolved in 1000 mL deionized water. (D) Sodium dichlorisocyanurate solution (hypochlorite component): 4 g sodium dichlorisocyanurate ($C_3N_3O_3Cl_2Na*2H_2O$) was dissolved in 1000 mL deionized water.

Solutions B and C were freshly premixed 2:1 (vol/vol) on the day of analysis. Reagent A (400 µL) was added into the microtiter plates, then 240 µL premixed reagent B/C was added, followed by 400 µL sample, and finally, 160 µL reagent D. The microtiter plates were covered and agitated, and after 60 minutes of reaction time, the blue-green indophenol dye was measured at 660 nm.

Results and Discussion

Figure 9:
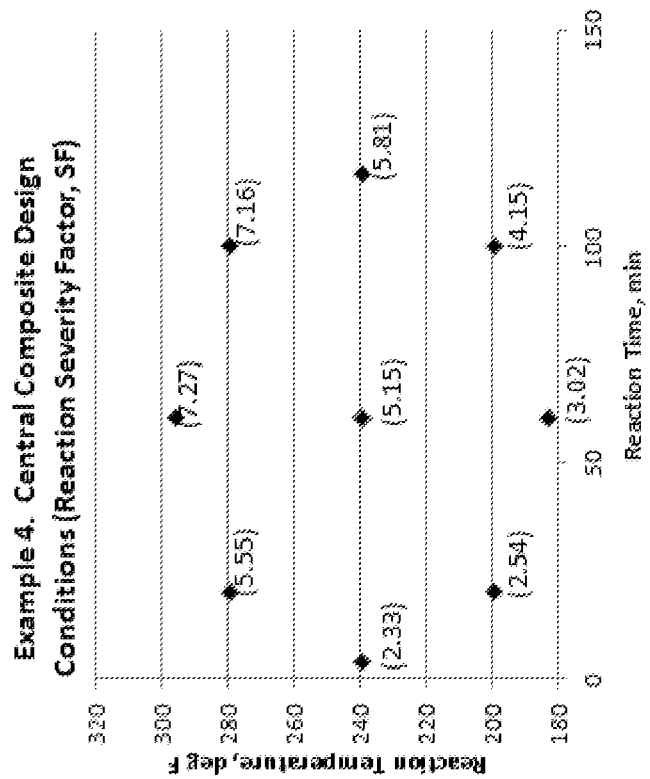
FIG. 9 is a chart showing central composite experimental design used in Example 4 to study the effects of time and temperature on hydrothermal fractionation.
Figure 11B:
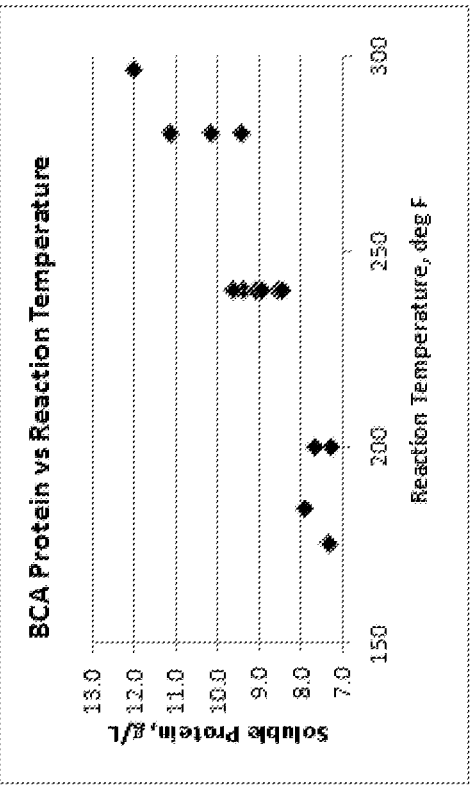
FIGS. 11A-11D are graphs of ammonia, soluble (BCA) protein, crude fat, and change in suspended solids versus thin stillage plotted against the reaction temperature for the designed experiment of Example 4.
Figure 11D:
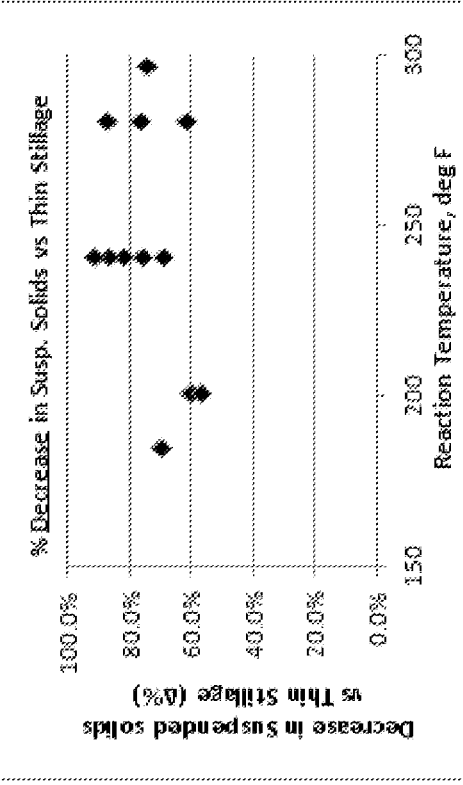
Figure 11A:
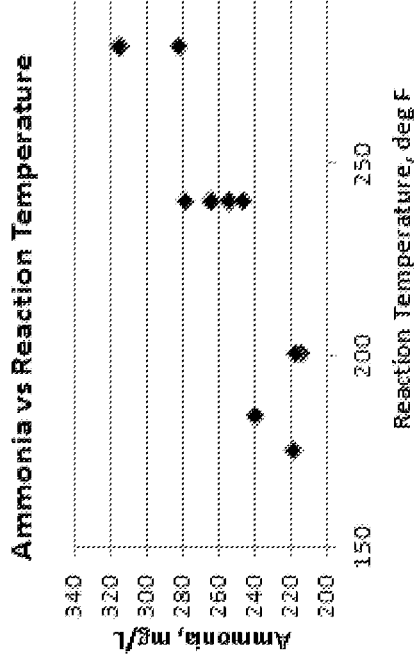
Figure 11C:
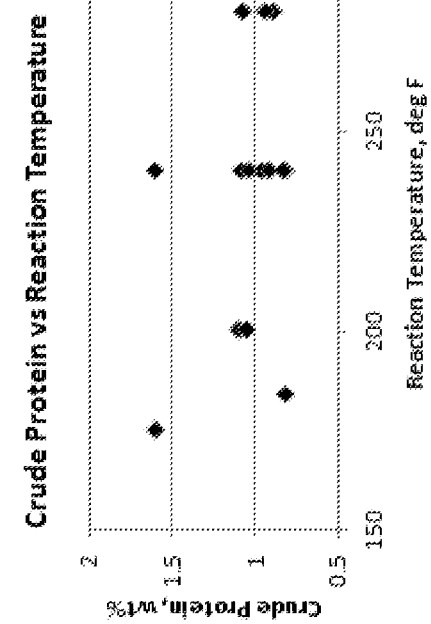

The DOE run conditions are depicted in FIG. 9. In the area of biomass thermal fractionation and lignocellulosic pretreatment, the concept of reaction severity has been applied to account for the combined effects of time and temperature. Overend et al. (Phil. Trans. R. Soc. London A, (1987) 321: 523-536,) developed the generalized severity parameter, $R_o$ shown below, where t is the reaction time and w expresses the temperature influence and is related to the average activation energy for hydrolysis reactions. The reaction severity factor, SF is taken as the natural logarithm of the generalized severity parameter and is a unit-less value (S. H. da Cruz et al., *J Ind Microbiol Biotechnol* (2012) 39:439-447).

$$Ro = \int_0^t \exp\left(\frac{T - Tref}{\omega}\right) dt,$$

which for an isothermal reaction becomes, $$Ro = \exp\left(\frac{T - Tref}{\omega}\right) xt$$

$$SF = \ln(Ro)$$

$T_{ref}$ was taken as 100 degrees C. (212 degrees F.) and a value of 14.75 was used herein as suggested by Overend et al. for aqueous/steam hydrolysis of biomass. Values for SF, the hydrothermal fractionation run conditions and analytical results are given in TABLE 5.

TABLE 5

| Sample | Reaction Time, min | Reaction Temp, F | Reaction Severity Factor, SF | Ammonia mg/L | Soluble BCA Protein, g/L | Crude Protein, wt % | Crude Fat wt % | Decrease in Total Solids vs Thin Stillage | % Decrease in Suspended Solids vs Thin Stillage |
|---|---|---|---|---|---|---|---|---|---|
| Thin Stillage (Feed) | n/a | n/a | 2.53* | 220 | 7.4 | 1.61 | 1.55 | 0.0% | 0.0% |
| Stickwater Samples | | | | | | | | | |
| 1** | 60 | 240 | 5.15 | 255 | 7.4 | 1.61 | 0.58 | 30.8% | 82.2% |
| 2a | 116 | 240 | 5.81 | 265 | 8.6 | 0.97 | 0.47 | 24.3% | 76.1% |
| 2b | 116 | 240 | 5.81 | 279 | 8.5 | 1.10 | 0.5 | 33.8% | 86.7% |
| 3 | 20 | 280 | 5.55 | 283 | 9.4 | 0.9 | 0.66 | 19.8% | 61.7% |
| 4 | 100 | 200 | 4.15 | 215 | 7.3 | 1.11 | 1.12 | 19.8% | 60.3% |
| 5 | 20 | 200 | 2.54 | 218 | 7.7 | 1.06 | 0.82 | 24.8% | 56.9% |
| 6** | 60 | 240 | 5.15 | 264 | 9.4 | 1.04 | 0.61 | 19.6% | 54.8% |
| 7** | 60 | 240 | 5.15 | 255 | 9.1 | 0.92 | 0.58 | 31.9% | 91.6% |
| 8a | 100 | 280 | 7.16 | 315 | 11.1 | 0.95 | 0.17 | 34.9% | 87.5% |
| 8b | 100 | 280 | 7.16 | 315 | 10.2 | 1.08 | 0.11 | 31.7% | 76.9% |
| 9 | 60 | 184 | 3.02 | 240 | 7.9 | 0.82 | 0.08 | 24.3% | 70.0% |
| 10 | 4 | 240 | 2.33 | 247 | 9.0 | 0.82 | 0.76 | 21.0% | 55.4% |
| 11 | 60 | 296 | 7.27 | 317 | 12.1 | 1.01 | 0.17 | 28.9% | 74.5% |
| 12** | 60 | 240 | 5.15 | 265 | 9.6 | 0.83 | 0.59 | 25.0% | 69.1% |
| Ctr Pt Avg | 60 | 240 | 5.15 | 260 | 7.9 | 1.1 | 0.59 | 26.8% | 74.4% |

*For comparison purposes, the time-temperature history and hence $R_{SF}$ for thin stillage was estimated by assuming 35 min at 185 degrees F. as a typical residence time and bottom temperature in the beer column.
**Center points of the DOE replicated four times.

FIGS. 10A-10D show various charts of the data from TABLE 5 plotted against the reaction severity factor, SF while FIGS. 11A-11D show various charts for the data plotted against reaction temperature. Although there is some scatter in the data, ammonia and soluble protein clearly increase in stickwater with increasing reaction severity or temperature. It is believed that hydrolysis reactions are contributing to the observed increases. Ammonia and protein are potential fermentation enhancers when stickwater is recycled as backset. Both crude fat (oil) and suspended solids show a decreasing trend with reaction severity. Since oil is associated with the solids, it is expected that crude fat should decrease as more suspended solids are removed. Hence increasing oil recovery can be expected with increasing reaction severity.

Example 5

Continuous Separation of Stickwater, Solids and Oil from Hydrothermally Fractionated Thin Stillage with a Three-Phase Decanter For the present EXAMPLE 5, thin stillage obtained from a commercial ethanol plant was continuously pumped at a rate of 3 gallons per minute through a series of Plate and Frame Heat Exchangers (PHEs) into a 150 gallon stirred reactor. The PHEs heated the stillage to 250 degrees F. The reactor's pressure was maintained at the saturation pressure of the stillage. The reactor had a working volume of 115 gallons and a mean residence time of 38 minutes. The conditioned stillage was continuously withdrawn from the reactor into a holding tank and pumped at approximately 3 gpm and 150 degrees F. to an Andritz three phase decanter centrifuge (Andritz model D2LC20C PC SA 3PH). Stickwater, oil and high solids fractions were collected. The starting thin stillage and stickwater were analyzed for solids and oil content.

Methods of Analysis

The AOAC analytical methods listed above were used in this example.

Results and Discussion

TABLE 6 shows a comparison of thin stillage and the stickwater fraction. It can be seen that the hydrothermal treatment conditions of 250 degrees F. and 38 minutes and separating the treated thin stillage to separation with a three phase decanter produced a stickwater fraction having low suspended solids and low residual oil.

TABLE 6

| | Thin Stillage | Stickwater |
|---|---|---|
| Total Solids (w/w) | 6.58 | 5.24 |
| Suspended solids (w/w) | 2.12 | 0.15 |
| Crude Fat (w/w) | 1.60 | 0.30 |

Example 6

Ethanol Fermentation Improved by Stickwater Produced by Hydrothermal Treatment of Thin Stillage at 285 Degrees F.

Dry-grind corn ethanol plants recycle their thin stillage to the front end of the plant to be used as make up water in the cook and fermentation processes. In this example, both thin stillage obtained from a commercial ethanol plant and stickwater prepared thereof were used as the basis for a fermentation medium to which anhydrous glucose was added as a carbon source. No other nutrients were added, thereby showing that the stickwater can be a superior media compared to thin stillage.

Procedures

Stickwater was prepared and collected as in EXAMPLE 1 at a hydrothermal treatment temperature of 285 degrees F.

Culture and Fermentation

The batch fermentations were started with an initial culture of a commercial ethanol producing *Saccharomyces cerevisiae* (Ethanol Red®, obtained from Fermentis div. of Lesaffre). Two batches of stickwater were produced from commercial thin stillage based on the methods described above, and the resultant stickwater from each batch were then compared to an original sample of thin stillage for ethanol fermentation performance. To a 1 liter sample of thin stillage or stickwater, approximately 200 grams of anhydrous glucose was added as the carbon source and allowed to dissolve. The resultant glucose/sample was added to an autoclaved 1.5 liter stirred reactor (Pyrex® Pro-Culture Spinner Flask (1.5 L); Corning, Corning, N.Y.) and the temperature of the fermentor was equilibrated to 82 degrees F. prior to inoculation.

Inoculum

The inoculum was prepared in a 250 ml sterile Erlenmeyer flask by addition of 1 gram of lyophilized yeast into 100 ml of filter sterilized 2% (w/w) malt extract broth and was incubated at 82 degrees F. for 30 minutes before use. From the inoculum, 5 ml was used to start the fermentations.

Batch Fermentation

An initial sample was taken prior to inoculation and frozen. The fermentation was done at 82 degrees F. with 110 rpm agitation. Fermentation vent locks were fitted to the fermenters at 1 hour after inoculation, to prevent oxygen from entering the vessel. At various time points, samples were removed and frozen prior to analysis via HPLC. After 48 hours the fermentations were stopped.

Methods of Analysis

HPLC analysis for ethanol, glucose (dextrose), and organic acids is based on NREL method LAP 015. Analysis was performed on a Phenomenex Rezex ROA-Organic acid column at 55 degrees C. using 0.005 N sulfuric acid as the eluent and flow rate set at 0.6 ml/min. The detection was via a UV/Vis detector set at 190 nm and CAD (Charged Aerosol Detector). Samples were unthawed, diluted, filtered through a 0.2 micron nylon filter. The injection volume was 20 e was 20 sol Detector). Samples were unthawed, diluted, and filtered through a 0.2 micron nylon filter. The injection volume was 20 μl and the samples were compared against standards.

Results and Discussion

TABLE 7 demonstrates that stickwater provides a superior fermentation medium for ethanol production as compared to thin stillage. Stickwater improved both the rate of ethanol production and yield of ethanol on dextrose versus untreated thin stillage. The theoretical mass yield of ethanol on dextrose is 0.5114 g/g [calculated as 2 mols ethanol*46.068 g/mol)/(1 mol dextrose*180.16 g/mol)=0.5114]. A yield in excess of 0.5114 g/g for both of the treated samples in this example indicates that the stickwater of the present invention provides nutrient value not supplied by untreated thin stillage, thus enhancing the value of stickwater as backset. Additionally this example shows that 100% of the produced stickwater can be recycled as backset without deleterious impact on fermentation performance.

TABLE 7

Ethanol Fermentation results with Stickwater versus Untreated Thin Stillage

| Fermentation Metric | Sample A | Sample B | Average of Treated Samples | Untreated Thin Stillage (Control) |
|---|---|---|---|---|
| Ethanol Production Rate (g ethanol/l/hr) | 1.97 | 1.95 | 1.96 | 1.67 |
| Ethanol yield (g/g dextrose utilized) | 0.517 | 0.529 | 0.523 | 0.435 |
| % of Theoretical Yield | 101.1% | 103.4% | 102.3% | 85.1% |

Example 7

Ethanol Fermentation Improved by Stickwater Produced by Hydrothermal Treatment of Thin Stillage at 240 Degrees F.

In this example, it will be shown that stickwater produced at a temperature of 240 degrees F. provides a beneficial media for ethanol fermentation.

Procedures

The thin stillage feed and resultant stickwater of DOE Condition 2 in Example 4 were used to prepare the fermentation media for this example. The hydrothermal treatment of DOE Condition 2 was for 116 minutes at 240 degrees F. and this condition was replicated twice (2a and 2b) to provide sufficient stickwater for fermentation. Two fermentation runs each were performed with the treated stickwater and thin stillage. All fermentation conditions, preparations and analyses were as described in Example 6.

Results and Discussion

TABLE 8 demonstrates that stickwater prepared by hydrothermal treatment of thin stillage at 240 degrees F. for 116 minutes provides a superior fermentation medium for ethanol production as compared to thin stillage. Additionally this example shows that 100% of the produced stickwater may be recycled as backset without deleterious impact on fermentation performance.

TABLE 8

Ethanol Fermentation results with Stickwater prepared by 240 degrees F. hydrothermal treatment versus Untreated Thin Stillage

| | Average of n = 2 Treated Samples | Average of n = 2 Untreated Thin Stillage samples (Control) |
|---|---|---|
| Dextrose used, g | 229.5 | 226.4 |
| Ethanol produced, g | 117.3 | 116.7 |
| % Theoretical yield of Ethanol on dextrose consumed | 97.5% | 88.5% |

Example 8

Fermentation of Thick Stillage

In this example, the flexibility of the present invention to produce advantageous stickwater from stillage of varying solids concentrations, i.e. thin stillage, thick stillage and whole stillage, is demonstrated. The advantage of whole stillage or thick stillage, prepared by filtration for example, is that they offer higher recoverable oil concentrations than thin stillage (reference TABLE 9 below).

Procedures

Whole stillage and thin stillage were obtained from a commercial ethanol plant. To produce stillage having a suspended solids concentration between that of whole and thin, whole stillage was filtered through a series nylon filter bags of decreasing pore size (1000, 600, 400, 100 microns). Filtrate from the 100 micron filter was taken as "thick" stillage. Samples of thin stillage, whole stillage, and thick stillage were analyzed for total solids, suspended solids, and oil. The resultant material was hydrothermally conditioned at 270 degrees F. for 40 minutes, and then separated to produce a stickwater fraction. The stickwater fraction was used as fermentation medium for ethanol production, as previously described in EXAMPLE 6.

Results and Discussion

Figure 12:
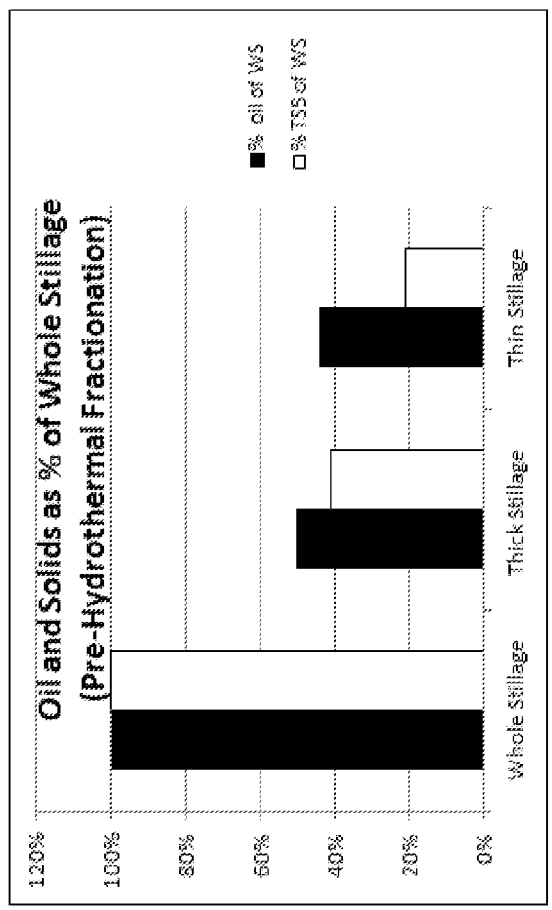
FIG. 12 is a graph of Oil and Total Suspended Solids as percentages of whole stillage for whole, thick, and thin stillage samples prior to hydrothermal fractionation.

TABLE 9 and FIG. 12 give oil and solids levels prior to hydrothermal treatment and illustrate that a significant percentage of the oil is associated with the suspended solids. Thus, a process which can flexibly treat high and low solids stillage streams will be advantageous. TABLE 10 shows that stickwater prepared by the present invention from any of the stillage concentrations can be used as fermentation media with no loss of performance. The ability to produce stickwater from thin, thick or whole stillage is an unexpected result of the present invention and can provide the ethanol producer with greater oil yield, advantageous fermentation yields and process flexibility.

TABLE 9

Oil and Solids prior to Hydrothermal Fractionation

|  | Whole Stillage | Thick Stillage | Thin Stillage |
| --- | --- | --- | --- |
| Total Suspended Solids (w/w) | 8.64 | 3.56 | 1.83 |
| Pre-Treatment Oil (as w/w % dry basis of Whole Stillage) | 1.53 | 0.77 | 0.68 |

TABLE 10

Ethanol Fermentation using Stickwater prepared from Whole Stillage, Filtered Whole Stillage and Thin Stillage.

| | Stickwater Source | | |
| --- | --- | --- | --- |
| | Whole Stillage | Thick Stillage | Thin Stillage |
| Dextrose Utilized(g/l) | 181.5 | 173.1 | 190.7 |
| Ethanol yield (g/g dextrose utilized) | 0.430 | 0.455 | 0.435 |
| % of Theoretical Yield | 84.1% | 89.0% | 85.1% |

Example 9

Analysis and Comparison of Stickwater and Thin Stillage as Fermentation Media for Other Microorganisms In this example, an oleaginous yeast, *Lipomyces starkeyi*, was chosen as the model microorganism for fermentation. *L. starkeyi* was chosen due to its ability to grow on a variety of carbon sources and nitrogen sources. Stickwater prepared by the present invention is compared to thin stillage.

Procedures

Stickwater was prepared and collected as in EXAMPLE 1.

Yeast and Fermentation

Both thin stillage and stickwater were sterile filtered through 0.2 micron cellulose acetate membrane prior to inoculation. *Lipomyces starkeyi* Y-11557 was obtained as ampoules of lyophilized solid from the USDA NRRL culture collection (NRRL, Lab Peoria, Ill.). The inoculum was prepared by adding the full ampoule of lyophilized yeast into a 250 mL sterile shake flask containing 100 mL of filter sterilized 2% malt extract medium and then grown for 24 hours at 25 degrees C. and 110 rpm agitation to produce cells in logarithmic growth phase. The fermentations were performed in sterile 1.5 liter stirred vessels (Pyrex® Pro-Culture Spinner Flask (1.5 L); Corning, Corning, N.Y.) charged with 1 liter of fermentation medium, air flow of 0.95 SLPM, agitation rate of 110 rpm and 80-82 degrees F. A 5 ml inoculum sample was used to start the fermentation and growth was then monitored for 48 hours.

Methods of Analysis

Samples were removed during the course of fermentation and analyzed for microscopic cell count and dry weight (AOAC method). Microscopic cell counts were performed with an Improved Neubauer Counting Chamber using serial dilutions in sterile water as the diluent.

Results and Discussion

In the present example, the stickwater and thin stillage samples were sterile filtered to prevent the potential contamination of the *L. starkeyi* fermentation batches by foreign micro-organisms. Filtration effectively removed all suspended solids greater than 0.2 μm. Hence the impact of soluble components and any residual ultra-fine suspended solids in the stickwater and thin stillage media is highlighted by this example. TABLE 6 shows the final (48 hours) dry weights of the Lipomyces grown on stickwater versus clarified thin stillage. The total dry weight of the biomass grown on stickwater was 28.6% higher than that grown on clarified thin stillage.

Figure 13:
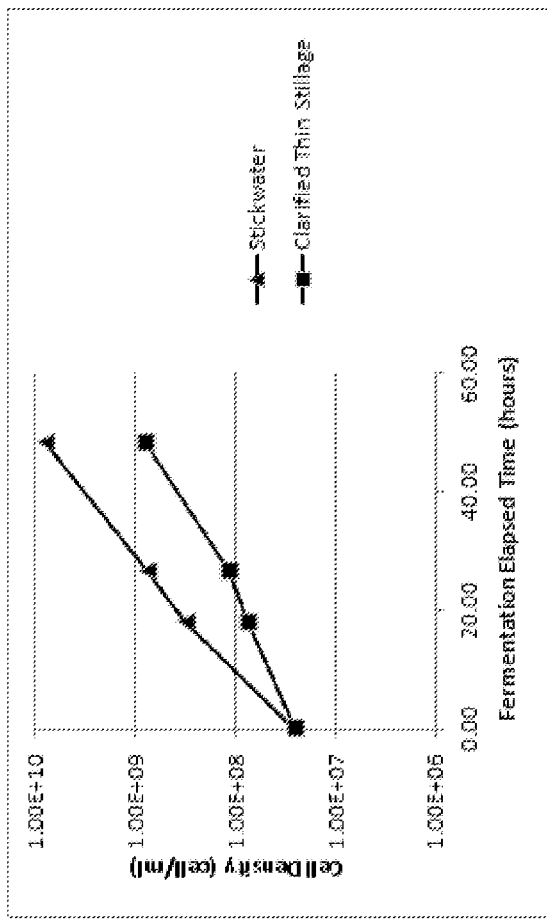
FIG. 13 is a semi-log plot of cell counts versus time for growth of *Lipomyces starkeyi* on stickwater versus thin stillage.

FIG. 13 shows the difference between Lipomyces grown on stickwater versus clarified thin stillage in total cell count. The graph shows that growth on filtered stickwater is much more rapid than growth on filtered thin stillage indicating that the soluble components and any residual ultra-fine suspended solids contained in stickwater provide an advantaged growth medium. Furthermore, this example shows that even fine filtration of thin stillage is not sufficient to provide the unique growth media properties provided by stickwater.

An ethanol plant could diversify its product lines by adding biomass fermentation utilizing stickwater as a medium. An economic advantage is anticipated due to the enhanced growth performance of stickwater versus thin stillage.

TABLE 6

Dry Weight comparison of *Lipomyces Starkeyi*

|  | Stickwater | Clarified Thin Stillage |
| --- | --- | --- |
| g/l Dry Weight | 3.01 | 2.34 |

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of improving fermentation, including the steps of:
   heating stillage to a temperature of 200° F. to 350° F. and holding the stillage at the temperature for 3 to 180 minutes and at a pressure at or above the saturation pressure of the stillage resulting in hydrothermally treated stillage including oil, a high protein solids fraction, and a stickwater fraction;
   removing from the hydrothermally treated stillage some of a composition of dissolved solids by a mechanism chosen from the group consisting of membranes, biological remediation, electro-dialysis, ion exchange, distillation, solvent extraction, and precipitation;
   after removal of some of a composition of dissolved solids, preparing a media that includes all or a portion of the hydrothermally treated stillage;
   and
   using the media in a process chosen from the group consisting of fermentation and biomass production.

2. The method of claim 1, further including the step of adding the hydrothermally treated stillage to an operation upstream of a fermentation step.

3. The method of claim 1, further including the step of cooling the hydrothermally treated stillage prior to use in fermentation media.

4. The method of claim 1, wherein the fermentation process produces an alcohol.

5. The method of claim 1, wherein the fermentation process produces a metabolite chosen from the group consisting of organic acids, alcohols, lipids, carbohydrates, proteins, and secondary metabolites.

6. The method of claim 5, further including the step of separating the metabolites from the fermentation media.

7. The method of claim 1, where the fermentation process is chosen from the group consisting of an anaerobic process and an aerobic process.

8. The method of claim 1, wherein the biomass is chosen from the group consisting of algae, bacteria, yeast, fungi, archae, and cultured cells.

9. The method of claim 1, wherein organic compounds in the hydrothermally treated stillage provide all or a portion of a carbon source.

10. The method of claim 1, wherein the hydrothermally treated stillage provides all or a portion of the nutrient requirements.

11. The method of claim 1, further including the step of adding at least one of a carbon source and nutrients to the media.

12. The method of claim 11, wherein the carbon source is chosen from the group consisting of dextrose, sucrose, fructose, xylose, arabinose, organic acids, glycerol, ethanol, carbon monoxide, carbon dioxide, and methane.

13. The method of claim 11, wherein the carbon source is derived from cellulosic material.

14. The method of claim 1, wherein the stillage is thin stillage.

15. The method of claim 14, further including the step of removing some or all of the solids from the thin stillage prior to or after said heating step.

16. The method of claim 1, wherein the stillage is whole stillage.

17. The method of claim 16, further including the step of removing some or all of the solids from the whole stillage prior to or after said heating step.

18. The method of claim 1, wherein the stillage is thick stillage.

19. The method of claim 18, wherein the thick stillage is produced by a method chosen from the group consisting of removal of water from stillage to concentrate solids, filtration of stillage, centrifugation of whole stillage under centrifuge operating conditions promoting transport of more solids into the centrate, addition of solids to thin stillage, particle size reduction of stillage to increase suspended solids in the feed to hydrothermal treatment, particle size reduction of grain or grain slurry to increase the suspended solids in the feed to hydrothermal treatment, and combinations thereof.

20. The method of claim 18, further including the step of removing some or all of the solids from the thick stillage prior to or after said heating step.

21. The method of claim 18, further including the step of removing solids from the stillage after said heating step.

22. The method of claim 21, wherein said removing solids step is performed by a mechanism chosen from the group consisting of centrifuges, decanting centrifuges, filter centrifuge, filters, membranes, hydrocyclone, quiescent decantation, dissolved air floatation, and flocculation.

23. The method of claim 1, further including the step of performing size reduction on all or a portion of the stillage prior to or after said heating step.

24. The method of claim 23, wherein the stillage is chosen from the group consisting of thin stillage, whole stillage, wet cake, and thick stillage.

25. The method of claim 23, further including the step of removing some of the solids from the stillage prior to or after said size reduction step.

26. The method of claim 25, wherein the removed solids are added back to the stillage after particle size reduction.

27. The method of claim 23, wherein the step of performing size reduction is performed with a mechanism chosen from the group consisting of colloid mills, disc mills, pin mills, jet mills, rotor-stator mixers, high-pressure homogenizers, and ultra-sonication.

28. The method of claim 1, wherein the stillage is concentrated stillage.

29. The method of claim 1, wherein the stillage is diluted stillage.

30. The method of claim 29, wherein the diluted stillage is diluted with a liquid chosen from the group consisting of water, process water, steam, and process vapors.

31. The method of claim 30, wherein the process vapors are chosen from the group consisting of flash steam, distillation vapor, distillation vapor condensate, evaporated thin stillage vapor, evaporated thin stillage vapor condensate, evaporated stickwater vapor, evaporated stickwater vapor condensate, dryer vapor, and dryer vapor condensate.

32. The method of claim 1, further including the step of removing some or all of the oil from the stillage before or after said heating step.

33. The method of claim 1, further including the step of recovering the biomass from the media.

34. The method of claim 1, further including the step of using fermentation effluent in additional fermentation processes.

35. The method of claim 34, wherein the additional fermentation process is alcohol fermentation.

36. The method of claim 35, further including the step of recovering biomass and/or metabolites prior to the additional fermentation process.

37. The method of claim 1, wherein said removing step further includes the step of removing from the hydrothermally treated stillage some of a composition chosen from the group consisting of suspended solids, oil, proteins, fiber, and ash.

38. The method of claim 37, wherein the suspended solids are removed by a mechanism chosen from the group consisting of centrifuges, decanting centrifuges, filter centrifuge, filters, membranes, hydrocyclone, quiescent decantation, dissolved air floatation, and flocculation.

39. The method of claim 37, further including the step of adding one or more agents to assist in the removal of solids chosen from the group consisting of acids, bases, minerals, polymeric flocculants, microparticulate settling aids, precipitation aids, and salts.

40. The method of claim 39, wherein the microparticulate settling aid is chosen from the group consisting of diatomaceous earth, bentonite, montmorillonite, colloidal silica borosilicate, and microsand.

41. The method of claim 39, further including the step of adjusting the temperature to assist in the removal of solids.

42. A method of improving fermentation, including the steps of:
   heating stillage to a temperature of 200° F. to 350° F. and holding the stillage at the temperature for 3 to 180 minutes and at a pressure at or above the saturation pressure of the stillage resulting in hydrothermally treated stillage including oil, a high protein solids fraction, and a stickwater fraction;
   removing from the hydrothermally treated stillage some of a composition of dissolved solids,
   wherein one or more agents chosen from the group consisting of acids, bases, minerals, polymeric flocculants, microparticulate settling aids, precipitation aids, and salts is added to assist in the removal of some of a composition of dissolved solids;
   after removal of some of a composition of dissolved solids, preparing a media that includes all or a portion of the hydrothermally treated stillage;
   and
   using the media in a process chosen from the group consisting of fermentation and biomass production.

43. The method of claim 42, wherein said removing step further includes the step of removing from the hydrothermally treated stillage some of a composition chosen from the group consisting of suspended solids, oil, proteins, fiber, and ash.

* * * * *